(12) United States Patent
Simonyan et al.

(10) Patent No.: US 10,889,698 B2
(45) Date of Patent: Jan. 12, 2021

(54) METHOD FOR MAKING WATER-ABSORBING POLYMER PARTICLES

(71) Applicant: The Procter & Gamble Company, Cincinnati, OH (US)

(72) Inventors: Arsen Simonyan, Schwalbach (DE); Juliane Kamphus, Schwalbach (DE); Josef Breu, Bayreuth (DE)

(73) Assignee: The Procter & Gamble Company, Cincinnati, OH (US)

( * ) Notice: Subject to any disclaimer, the term of this patent is extended or adjusted under 35 U.S.C. 154(b) by 319 days.

(21) Appl. No.: 15/954,644

(22) Filed: Apr. 17, 2018

(65) Prior Publication Data

US 2018/0305518 A1    Oct. 25, 2018

(30) Foreign Application Priority Data

Apr. 19, 2017   (EP) ................................ 17167079

(51) Int. Cl.
| | | |
|---|---|---|
| *C08J 3/12* | (2006.01) | |
| *C08K 3/34* | (2006.01) | |
| *A61L 15/60* | (2006.01) | |
| *A61L 15/18* | (2006.01) | |
| *C08J 3/20* | (2006.01) | |
| *C08J 3/24* | (2006.01) | |
| *A61L 15/24* | (2006.01) | |

(52) U.S. Cl.
CPC .............. *C08K 3/346* (2013.01); *A61L 15/18* (2013.01); *A61L 15/24* (2013.01); *A61L 15/60* (2013.01); *C08J 3/12* (2013.01); *C08J 3/203* (2013.01); *C08J 3/245* (2013.01); *C08J 2333/02* (2013.01); *C08K 2201/005* (2013.01)

(58) Field of Classification Search
CPC ......... C08K 3/346; A61L 15/18; A61L 15/24; A61L 15/60; C08J 3/12; C08J 3/203; C08J 3/245
USPC ........................................................ 524/798
See application file for complete search history.

(56) References Cited

U.S. PATENT DOCUMENTS

| | | | |
|---|---|---|---|
| 4,666,983 A | 5/1987 | Tsubakimoto et al. | |
| 5,331,059 A | 7/1994 | Engelhardt et al. | |
| 5,409,771 A | 4/1995 | Dahmen et al. | |
| 5,607,414 A | 3/1997 | Richards et al. | |
| 5,700,254 A | 12/1997 | McDowall et al. | |
| 5,731,365 A | 3/1998 | Engelhardt et al. | |
| 5,837,789 A | 11/1998 | Stockhausen et al. | |
| 6,143,821 A | 11/2000 | Houben | |
| 6,472,478 B1 | 10/2002 | Funk et al. | |
| 6,503,979 B1 | 1/2003 | Funk et al. | |
| 6,559,239 B1 | 5/2003 | Riegel et al. | |
| 6,657,015 B1 | 12/2003 | Riegel et al. | |
| 6,911,499 B1 | 6/2005 | Brehm et al. | |
| 7,183,360 B2 | 2/2007 | Daniel et al. | |
| 7,199,211 B2 | 4/2007 | Popp et al. | |
| 7,250,481 B2 | 7/2007 | Jaworek et al. | |
| 7,652,111 B2 | 1/2010 | Hermeling et al. | |
| 7,687,596 B2 | 3/2010 | Hermeling et al. | |
| 7,754,822 B2 | 7/2010 | Daniel et al. | |
| 7,772,420 B2 | 8/2010 | Hermeling et al. | |
| 8,581,019 B2 | 11/2013 | Carlucci et al. | |
| 2003/0105190 A1 | 6/2003 | Diehl et al. | |
| 2005/0165208 A1 | 7/2005 | Popp et al. | |
| 2007/0093767 A1 | 4/2007 | Carlucci et al. | |
| 2008/0242817 A1 | 10/2008 | Ducker et al. | |
| 2009/0318884 A1 | 12/2009 | Meyer et al. | |
| 2011/0015296 A1 | 1/2011 | Meyer et al. | |
| 2012/0157622 A1 | 6/2012 | Lindner et al. | |

(Continued)

FOREIGN PATENT DOCUMENTS

| | | |
|---|---|---|
| CN | 101712785 | 5/2010 |
| DE | 10204937 A1 | 8/2003 |

(Continued)

OTHER PUBLICATIONS

International Search Report, PCT/US2018/027706, dated Jun. 14, 2018, (15 pages).

*Primary Examiner* — Hannah J Pak
(74) *Attorney, Agent, or Firm* — Brian M. Bolam

(57) ABSTRACT

A method for making water-absorbing polymer particles is provided and includes providing crosslinkers, polymerizable monomers and inorganic solid particles. The average closest distance between two neighboring crosslinkers ($R_{XL}$) in a water-absorbing polymer particle for a specific X-load of the water-absorbing polymer particle is calculated via the formula below:

$$Rxl = \left( \frac{\left( \frac{1}{\text{rho\_dry}} + \frac{\text{x\_L}}{\text{rho\_liq}} \right)}{N_A \cdot \sum_i \frac{\text{w\_xl}_i}{\text{Mr\_CXL}_i}} \right)^{\frac{1}{3}} \quad (I)$$

with x_L being the amount of liquid absorbed in the water-absorbing polymer particle in g liq/g water-absorbing polymer particle, rho_liq being the density at room temperature of the fluid that swells the water-absorbing polymer particle (generally saline of 0.9% w NaCl) in g/cm$^3$, rho_dry being the true density of the dry water-absorbing polymer particle in g/cm$^3$, Mr_CXL being the molar mass of the crosslinkers in g/mol, w_xl being the weight ratio of crosslinkers in dry water-absorbing polymer particle, $N_A$ being the Avogadro's number in mol$^{-1}$.

17 Claims, 9 Drawing Sheets

(56) References Cited

U.S. PATENT DOCUMENTS

2018/0303968 A1* 10/2018 Simonyan .............. C08K 3/346
2019/0298587 A1* 10/2019 Ashraf ................... B32B 5/022
2019/0380887 A1* 12/2019 Ashraf .............. A61F 13/51108

FOREIGN PATENT DOCUMENTS

| EP | 083022 | 7/1983 |
|----|--------|--------|
| EP | 149880 A2 | 7/1985 |
| EP | 547847 | 6/1993 |
| EP | 559476 A1 | 9/1993 |
| EP | 632068 A1 | 1/1995 |
| EP | 937736 A2 | 8/1999 |
| WO | WO9015830 | 12/1990 |
| WO | WO93021237 A1 | 10/1993 |
| WO | WO200059430 A1 | 10/2000 |
| WO | WO0145758 A1 | 6/2001 |
| WO | WO0232962 A2 | 4/2002 |
| WO | WO02067809 A2 | 9/2002 |
| WO | WO2006082242 A2 | 8/2006 |
| WO | WO2006083584 | 8/2006 |
| WO | WO2006097389 A2 | 9/2006 |
| WO | WO2009155265 | 12/2009 |
| WO | WO2012170778 | 12/2012 |

* cited by examiner

METHOD FOR MAKING WATER-ABSORBING POLYMER PARTICLES

FIELD OF THE INVENTION

The invention relates to a method for making water-absorbing polymer particles where the average closest distance between two crosslinkers for a specific X-load of a given water-absorbing polymer particle is calculated via a specific formula. The invention also relates to water-absorbing polymer particles obtained via the method herein and to an absorbent article comprising the water-absorbing polymer particles obtained via the method herein. The absorbent articles include, but are not limited to baby diapers, training pants, feminine hygiene sanitary pads and adult incontinence products.

BACKGROUND OF THE INVENTION

An important component of a disposable absorbent article such as a diaper is an absorbent core including water-absorbing polymer particles. This water-absorbing polymer particle ensures that large amounts of bodily fluids, e.g. urine, can be absorbed by the article during its use and locked away, thus providing low rewet and good skin dryness. Especially useful water-absorbing polymer particles are often made by initially polymerizing unsaturated carboxylic acids or derivatives thereof, such as acrylic acid, alkali metal (e.g. sodium and/or potassium) or ammonium salts of acrylic acid, alkyl acrylates, and the like.

These water-absorbing polymer particles need to have adequately high absorption capacity, as well as adequately high gel strength. Absorption capacity needs to be sufficiently high to enable the absorbent polymer to absorb significant amounts of the aqueous body fluids encountered during use of the absorbent article. At the same time, the water-absorbing polymer particles need to have a good permeability for fluid transport through the swollen crosslinked polymer particles.

The properties of water-absorbing polymer particles have been characterized in various ways. The absorbent capacity (CRC) in grams of liquid per gram of water-absorbing polymer particles has been used, as well as the absorption speed as measured by the Free Swell Rate (FSR) and their permeability as measured by the Urine Permeability Measurement (UPM) test.

Low molecular weight polymer chains that are not incorporated into the crosslinked polymer network exist in the water-absorbing polymer particle and are called "extractables". These chains can be extracted from the crosslinked polymer network when the water-absorbing polymer particles are swollen in excess liquid. The "extractables" do not contribute to the water-absorbing polymer particles performance.

Moreover, the "extractables" increase the ionic strength in the environment of the water-absorbing polymer particles due to their charged groups and negatively impact the absorption capacity of the water-absorbing polymer particles. Therefore, the quantity of "extractables" is important in determining the optimum performance of the water-absorbing polymer particles. There is a need to provide water-absorbing polymer particles with a low quantity of "extractables".

Water-absorbing polymer particles with relatively high permeability can be made by increasing the level of internal crosslinking or surface crosslinking, which increases the resistance of the swollen gel against deformation by an external pressure and decrease the number of "extractables". However, increasing the level of internal crosslinking or surface crosslinking typically reduce the absorption capacity of the water-absorbing polymer particles.

On the contrary, decreasing the level of internal crosslinking or surface crosslinking in water-absorbing polymer particles leads to high absorption capacity of the water-absorbing polymer particles but also to a high number of "extractables" and a relatively low permeability.

Therefore, there is a need to provide water-absorbing polymer particles that presents a right balance between having high absorption capacity, high permeability and a low number of "extractables".

It is desirable to find a method for making water-absorbing polymer particles with improved performances in terms of capacity and permeability while having a low quantity of "extractables".

SUMMARY OF THE INVENTION

The present invention provides a method for making water-absorbing polymer particles by providing crosslinkers, polymerizable monomers and inorganic solid particles. The average closest distance between two neighboring crosslinkers ($R_{XL}$) in a water-absorbing polymer particle for a specific X-load of the water-absorbing polymer particle is calculated via the formula below:

$$Rxl = \left( \frac{\left( \frac{1}{rho\_dry} + \frac{x\_L}{rho\_liq} \right)}{N_A \cdot \sum_i \frac{w\_xl_i}{Mr\_CXL_i}} \right)^{\frac{1}{3}} \quad (I)$$

with x_L being the amount of liquid absorbed in the water-absorbing polymer particle in $g_{liq}/g_{water-absorbing\ polymer\ particle}$, rho_liq being the density at room temperature of the fluid that swells the water-absorbing polymer particle (generally saline of 0.9% w NaCl) in $g/cm^3$, rho_dry being the true density of the dry water-absorbing polymer particle in $g/cm^3$, Mr_CXL being the molar mass of the crosslinkers in g/mol, w_xl being the weight ratio of crosslinkers in dry water-absorbing polymer particle, $N_A$ being the Avogadro's number in $mol^{-1}$.

The average closest distance between two neighboring crosslinkers ($R_{XL}$) at 20 g/g X-load of the water-absorbing polymer particle obtained via the formula above is at least as high as an average size of the inorganic solid particles or higher than an average size of the inorganic solid particles.

The average closest distance between two neighboring crosslinkers ($R_{XL}$) at 20 g/g X-load of the water-absorbing polymer particle is from 3 to 100 nm.

The invention also relates to the water-absorbing polymer particles obtained by the method according to the invention.

The invention also relates to an absorbent article comprising the water-absorbing polymer particles obtained via the method described herein.

The formula above determines the average closest distance between two neighboring crosslinkers ($R_{XL}$) in a water-absorbing polymer particle for a specific X-load of the water-absorbing polymer particle in order to obtain water-absorbing polymer particles with good performances in terms of permeability and capacity and with a low quantity of "extractables".

The average closest distance between two neighboring crosslinkers ($R_{XL}$) in the water-absorbing polymer particle at 20 g/g X-load of the water-absorbing polymer particle obtained via the formula above is at least as high as an average size of the inorganic solid particles or higher than an average size of the inorganic solid particles.

Therefore, the inorganic solid particles present an average range of size that can fit the average closest distance between two neighboring crosslinkers ($R_{XL}$) in the water-absorbing polymer particles at 20 g/g X-load of the water-absorbing polymer particles.

The inorganic solid particles that fit the average closest distance between two neighboring crosslinkers ($R_{XL}$) may act as barrier particles in the crosslinked polymer network such that the diffusion of the "extractables" outside of the crosslinked polymer network is limited but the influx of fluid through the crosslinked polymer network is not slowed down significantly by the inorganic solid particles.

The water-absorbing polymer particles obtained via the method of the invention may have a relatively low amount of "extractables". The method of the invention may improve the permeability and the capacity of the water-absorbing polymer particles.

Therefore, the water-absorbing polymer particles show good performance properties. Especially, the surface-coated water-absorbing polymer particles may have a high permeability, a good absorption capacity and a good effective capacity.

DETAILED DESCRIPTION OF THE INVENTION

Definition

Figure 1:
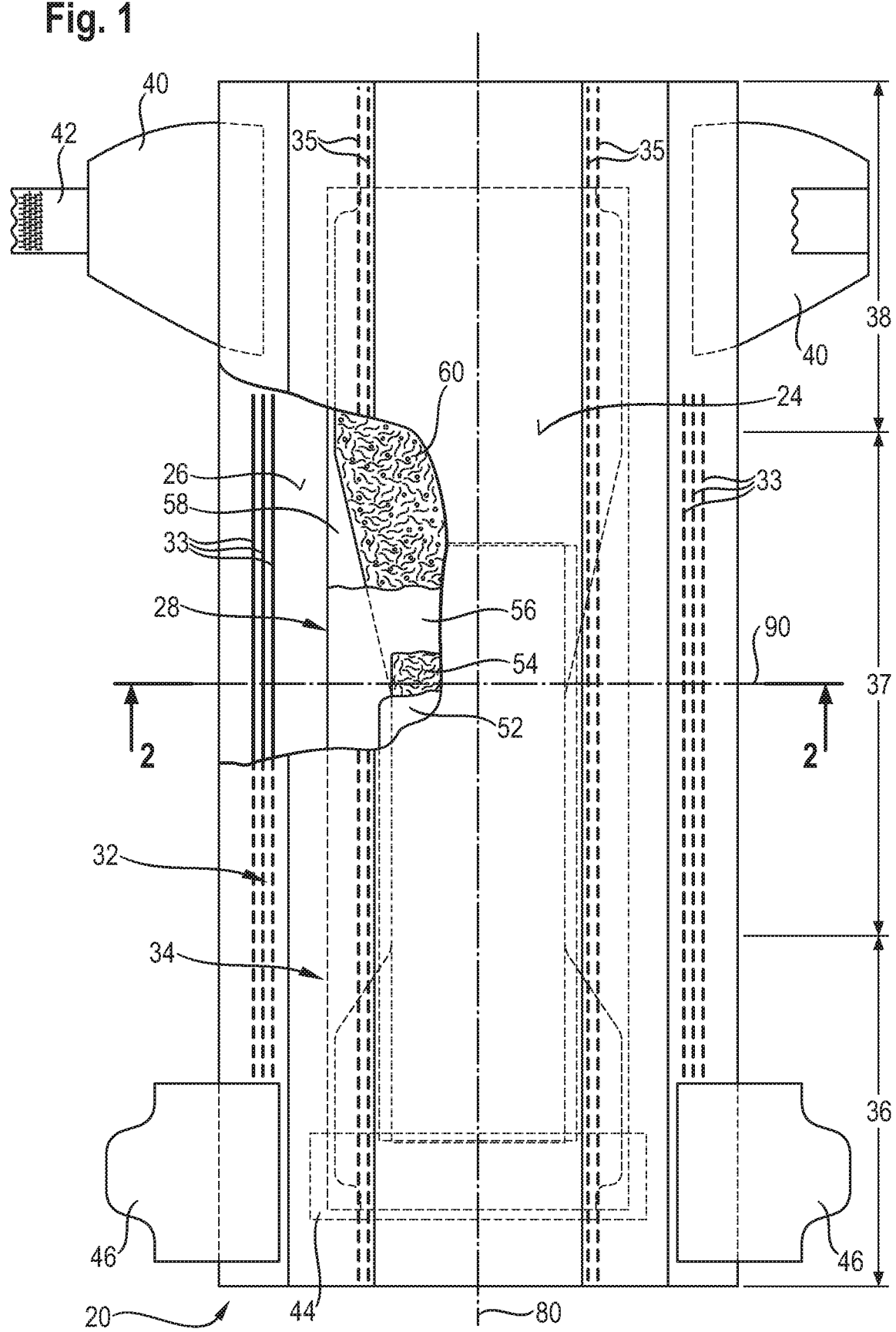
FIG. 1 is a top view of an exemplary absorbent article in the form of a diaper, which may comprise the water-absorbing polymer particles of the present invention, with some layers partially removed.

The term "Absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants, inserts, feminine care absorbent articles such as sanitary napkins or pantiliners, and the like. The term "exudates" includes, but is not limited to, urine, blood, vaginal discharges, sweat and fecal matter. Preferred absorbent articles of the present invention are disposable absorbent articles, more preferably disposable diapers and disposable pants.

"Disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

"Diaper" and "pant" refers to an absorbent article generally worn by babies, infants and incontinent persons about the lower torso so as to encircle the waist and legs of the wearer and that is specifically adapted to receive and contain urinary and fecal waste. In a pant, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasably) attaching the longitudinal edges of the first and second waist region to each other on both sides by a suitable fastening system.

The term "true density" refers to the density of the water-absorbing polymer particle that make up a particulate solid in contrast to the bulk density, which measures the average density of a large volume of the water-absorbing polymer particle in a specific medium (usually air).

The term "size of the inorganic solid particle" refers to the largest dimension of an exfoliated inorganic solid particle such as clay platelet.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

Water-Absorbing Polymer Particles

"Water-absorbing polymers" or "Superabsorbent polymers" refer to absorbent material which are crosslinked polymeric materials that can absorb at least 10 times their weight of an aqueous 0.9% saline solution as measured using the Centrifuge Retention Capacity (CRC) test method (EDANA method NWSP 241.0.R2). These polymers are typically used in particulate forms ("Water-absorbing polymer particles" or "Superabsorbent polymers particles") so as to be flowable in the dry state. The term "particles" refers to granules, fibers, flakes, spheres, powders, platelets and other shapes and forms known to persons skilled in the art of water-absorbing polymer particles.

Preferred water-absorbing polymer particles of the present invention are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

Typically, the water-absorbing polymer particles comprise crosslinked polymers, preferably lightly crosslinked hydrophilic polymers. While these polymers may in general be non-ionic, cationic, zwitterionic or anionic, the preferred polymers are cationic or anionic.

Preferably, water-absorbing polymer particles comprise acid polymers which contain a multiplicity of acid functional groups such as carboxylic acid groups or their salts, preferably sodium salts.

Preferably, the water-absorbing polymer particles comprise crosslinked polymers of polyacrylic acids or their salts or polyacrylates or derivatives thereof.

Exemplary water-absorbing polymer particles of the prior art are for example described in WO2006/083584, WO2007/047598, WO2007/046052, WO2009/155265, WO2009/155264.

The water-absorbing polymer particles can be spherical shaped water-absorbing polymer particles or ellipsoidal shaped water-absorbing polymer particles or irregular shaped water-absorbing polymer particles. Preferably, the water-absorbing polymer particles have a spherical or ellipsoid shape.

Preferably water-absorbing polymer particles have a particle size distribution in the range from 45 µm to 850 µm, or more preferably from 100 µm to 850 µm or 150 µm to 710 µm or 150 µm to 500 µm or 150 µm to 300 µm as measured according to EDANA method WSP 220.2-05.

Preferably, water-absorbing polymer particles are obtainable by polymerization of a monomer solution comprising
i) at least one polymerizable ethylenically unsaturated acid-functional monomer,
ii) at least one crosslinker,
iii) if appropriate one or more polymerizable ethylenically and/or allylically unsaturated monomers copolymerizable with i) and
iv) if appropriate one or more water-soluble polymers onto which the monomers i), ii) and if appropriate iii) can be at least partially grafted,
v) at least one polymerization initiator system, wherein the base polymer obtained thereby is dried, and—if appropriate—is subsequently treated with
vi) at least one post-crosslinker to be post-crosslinked (i.e. surface crosslinked).

Polymerizable Monomers

Polymerizable monomers i) may include for example ethylenically unsaturated carboxylic acids or their salts, such as acrylic acid, methacrylic acid, maleic acid, fumaric acid, tricarboxy ethylene, itaconic acid, ethylenically unsaturated phosphonic acid and ethylenically unsaturated sulfonic acid or their salts, or derivatives thereof, such as acrylamide with 2-acrylamido-2-methylpropane sulfonic acid, methacrylamide, acrylic esters and methacrylic esters.

Preferably, the polymerizable monomers are selected from the group consisting of ethylenically unsaturated carboxylic acids such as methacrylic acid or its salts, or acrylic acid or its salts, ethylenically unsaturated phosphonic acids or their salts, ethylenically unsaturated sulfonic acids or their salts, or mixtures thereof.

Acrylic acid or its salts and methacrylic acid or its salts are particularly preferred monomers. Acrylic acid or its salts is most preferable.

Examples of ethylenically unsaturated monomers iii) which are copolymerizable with the polymerizable monomers i) may be acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Water-soluble polymers iv) onto which the polymerizable monomers i), the crosslinkers ii) and if appropriate ethylenically unsaturated monomers iii) can be at least partially grafted may include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide.

The preparation of a suitable base polymer and also further useful polymerizable monomers i) are described in DE-A 199 41 423, EP-A 686 650, WO 01/45758 and WO 03/14300.

Crosslinkers

The water-absorbing polymer particles are crosslinked, i.e., the polymerization is carried out in the presence of compounds having two or more polymerizable groups which can be free-radically copolymerized into the crosslinked polymers network. Crosslinkers ii) may include for example ethylene glycol dimethacrylate, diethylene glycol diacrylate, polyethylene glycol di(meth)acrylate) with molar masses between 200 and 2000 Da, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in the DE-A 103 31 450, mixed acrylates which, as well as acrylate groups, comprise further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962.

Preferably, the crosslinkers ii) comprise acrylate or acrylamide groups.

Preferably, the crosslinkers ii) are diacrylated, dimethacrylated, triacrylated or trimethacrylated multiply ethoxylated and/or propoxylated glycerols. Di- and/or triacrylates of 3- to 10-tuply ethoxylated glycerol are particularly advantageous. More preferably, the crosslinkers ii) are di- or triacrylates of 1- to 5-tuply ethoxylated and/or propoxylated glycerol.

Neutralizing Agents

Neutralizing agents can be used, such as alkali metal hydroxides, alkali metal oxides, alkali metal carbonates or alkali metal bicarbonates and also mixtures thereof. Neutralizing agents may be ammonia, or amines derivatives, such as ethanolamine, diethanolamine, triethanolamine or dimethylaminoethanolamine. Sodium and potassium can be used as alkali metal salts. Preferably, neutralizing agents are sodium hydroxide, sodium carbonate or sodium bicarbonate and also mixtures thereof. Typically, neutralization is achieved by admixing the neutralizing agent as an aqueous solution or as an aqueous dispersion or else as a molten or as a solid material. The acid groups of the base polymers obtained are typically 0-100 mol %, preferably 25-100 mol %, more preferably 65-90 mol % and most preferably 68-80 mol % neutralized.

Polymerization Initiator System

A polymerization initiator system v) is used in order to initiate the polymerization.

This polymerization initiator system may be added in solid or liquid form, for example as a solution or dispersion in a liquid such as an aqueous liquid, e.g. water.

This polymerization initiator system may comprise more than one type of compound to initiate the polymerization, or it may comprise a single type of compound.

The polymerization initiator system may include an activator, such as an activator compound or, for example, heat or radiation, including light radiation. Alternatively, no activation may be needed.

The polymerization initiator system can be appropriately selected from conventional (e.g. radical) polymerization initiators (and optional catalysts). Materials which display good water dispersibility/solubility are preferred. The polymerization initiator system may include peroxides, hydroperoxides, hydrogen peroxide, persulfates, azo compounds and redox initiators. Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Preferred azo compounds include 2,2'-azobisisobutyronitrile, 2,2'-azobis(2,4-dimethylvaleronitrile) and 2,2'-azobis (4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane)dihydrochloride, 2,2'-azobis [2-(2-imidazolin-2yl)propane] dihydrochloride and 2,2'-azobis[2-(5-methyl-2-imidazolin-2-yl)propane] dihydrochloride. Very particular preference is given to 2,2'-azobis [2-(2-imidazolin-2-yl)propane] dihydrochloride and 2,2'-azobis [2-(5-methyl-2-imidazolin-2yl)propane] dihydrochloride.

More particularly, the polymerization initiator system v) may be persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid. A mixture of two or more polymerization initiators may be used, for example one of the class of azo-compounds and one of the class of peroxo or peroxide compounds. This is believed to ensure fast polymerization. As described in US2008/242817, the use of azo compound initiator or redox initiators is advantageous for directing the rate of polymerization.

The polymerization initiator system may be introduced at a level of at least 0.001% by weight of the polymerizable monomers, preferably at least 0.01%, more preferably at least 0.02%, up to 0.1%, preferably up to 0.05% by weight of the polymerizable monomers.

The polymerization rate can be controlled through the identity and amount of the polymerization initiator compound used and the temperature used.

A polymerization catalyst may also be present, such as for example TMEDA (N,N,N',N' tetramethylethylenediamine). The polymerization of the polymerizable monomers may be highly exothermic, and hence, the polymerization liquid may be cooled during polymerization.

Surface Crosslinking

The water-absorbing polymer particles can be post-crosslinked (i.e. surface crosslinked). Preferably, the water-absorbing polymer particles are surface crosslinked. Post-crosslinkers vi) may include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. Useful post-crosslinkers vi) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by DE-A 103 34 584 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the base polymer or onto the dry water-absorbing polymer particles. Spraying is followed by thermal drying, and the post-crosslinking reaction can take place not only before but also during or after drying. Preferred post-crosslinkers vi) are amide acetals, carbamic esters, polyhydric alcohols like diols or polyols, cyclic carbonates or bisoxazolines.

At least one post-crosslinker vi) may be used in an amount of about 1.50 wt. % or less, preferably not more than 0.50% by weight, more preferably not more than 0.30% by weight and most preferably in the range from 0.001% and 0.15% based on the dry weight of the water-absorbing polymer particles.

The aqueous post-crosslinking solution, as well as the at least one post-crosslinker vi), can further comprise a co-solvent. Co-solvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol, 1,3-propanediol or 1,4-butanediol, ketones, such as acetone, or carboxylic esters, such as ethyl acetate.

The total amount of post-crosslinking solution based on the base polymer may be in the range from 0.3% to 15% by weight and preferably in the range from 2% to 6% by weight.

The water-absorbing polymer particles can have in the dry state a particle size distribution in the range from 45 μm to 1000 μm according to standard PSD test method (EDANA method WSP 220.2-05). Preferably water-absorbing polymer particles have a particle size distribution in the range from 45 µm to 850 µm, or more preferably from 100 µm to 850 µm or 150 µm to 710 µm or 150 µm to 500 µm or 150 µm to 300 µm.

Surface Treatment

The water-absorbing polymer particles may be coated with a surface treatment.

The coating may be done before, during or after post-crosslinking.

Such coating with one or more coating agent(s) makes it possible to achieve additional effects, such as a reduced tendency to cake, improved processing properties or a further enhanced permeability.

The surface treatment may comprise water soluble polyvalent metal salts, water-insoluble metal phosphates and inorganic particles, for example silica, clay, or mica.

Preferably, water soluble polyvalent metal salts are aluminum sulfate, aluminum nitrate, aluminum chloride, potassium aluminum sulfate, sodium aluminum sulfate, magnesium sulfate, magnesium citrate, magnesium lactate, zirconium sulfate, zirconium lactate, iron lactate, iron citrate, calcium acetate, calcium propionate, calcium citrate, calcium lactate, strontium lactate, zinc lactate, zinc sulfate, zinc citrate, aluminum lactate, aluminum acetate, aluminum formiate, calcium formiate, strontium formiate, strontium acetate. They may be used as surface treatment for the precursor water-absorbing polymer particles in order to impart a high passive fluid transport (UPM) by homogeneously coating the surface of the water-absorbing polymer particles.

Suitable water-insoluble metal phosphates may be selected from the group of pyrophosphates, hydrogen phosphates and phosphates of calcium, of magnesium, of strontium, of barium, of zinc, of iron, of aluminum, of titanium, of zirconium, of hafnium, of tin, of cerium, of scandium, of yttrium or of lanthanum, and also mixtures thereof.

Suitable inorganic particles may be applied as powders or aqueous dispersions. Inorganic particles may be selected from the group of silica, fumed silica, colloidal dispersed silica, titaniumdioxide, aluminum- and magnesiumoxide, zinc oxide, clay. Silica may be hydrophilic or hydrophobic. For example, silica is known in the art to improve the absorption speed of the precursor water-absorbing polymer particles.

The surface treatment may also be selected from the group of film-forming polymers and/or elastic polymers and/or elastic film-forming polymers. Such surface treatment may be applied in order to form a complete coating on the water-absorbing polymer particles. The term 'film-forming' means that the respective polymer can readily be made into a film, i.e. layer or coating, e.g. a homogeneous coating on the particle, upon evaporation of the solvent in which it is dissolved or dispersed. The polymer may for example be thermoplastic or crosslinked. Suitable film-forming polymers may exhibit elastic physical properties. The elastic and elastic film-forming agents/polymers suitable as coating agents herein are disclosed in U.S. Pat. No. 5,731,365 and in EP 0703265, and also in WO 2006/082242 and WO 2006/097389.

Inorganic Solid Particles

The water-absorbing polymer particles comprise inorganic solid particles.

In the method for making water-absorbing polymer particles, the inorganic solid particles may be dispersed in a carrier liquid, such as an aqueous carrier liquid before being mixed with the polymerizable monomers and crosslinkers.

The dispersion of inorganic solid particles may be typically a homogeneous dispersion of inorganic solid particles. The carrier liquid may be water or a mixture of water and an organic liquid. The inorganic solid particles dispersion may preferably comprise very small amounts of aggregated inorganic solid particles, but or preferably no aggregated inorganic solid particles, so the dispersion of inorganic solid particles may be free of aggregated inorganic solid particles.

The concentration of inorganic solid particles in a carrier liquid may be less than 20% by weight of the dispersion, or less than 10% by weight of the dispersion, or less than 5% by weight of the dispersion or less than 1% by weight of the dispersion.

Inorganic solids particles may be clay particles. The clay particles may be in the form of platelets, e.g. exfoliated or individual clay particles in the form of platelets, having a largest dimension and a smallest dimension. For example, the largest dimension to smallest dimension ratio may be at least 2:1 or at least 10:1 or at least 25:1, up to 200:1 or up to 500:1. Preferably, the inorganic solid particles are clay platelets.

The clays may be partially exfoliated in a dispersion of clays in a carrier liquid or completely exfoliated.

Clay and Clay Platelets

The water-absorbing polymer particles may comprise clay platelets as inorganic solid particles. The clay platelets are preferably homogeneously dispersed in a carrier liquid, e.g. so that there is no significant aggregation/flocculation of the clay platelets (e.g. just prior to polymerization, e.g., at the temperature/pressure conditions of polymerization). Clay platelets have edge surfaces also referred to as "edges" and opposing basal platelet surfaces also referred to as "surfaces".

Examples of suitable clay platelets are selected from the group consisting of kaolinite such as kaolin, illite such as glauconite, or smectite or montmorillonite including hectorite, laponite (i.e. synthetic clay), saponite, vermiculite or mixtures thereof.

Preferably, the inorganic solid particles are montmorillonite, hectorite, laponite or mixtures thereof.

Preferably, the inorganic solid particles are laponite.

These clay platelets are often referred to as water swelling; however, it should be noted that, in the present invention the clay platelets are present as substantially individual clay platelets and then, they are no longer water swelling.

The clay platelets may be surface and/or edge-modified.

The clay platelets and the surface and/or edge-modified clay platelets in a carrier liquid may have a weight average largest particle size dimension (length) of less than 800 nm, preferably less than 500 nm, more preferably less than 300 nm, more preferably less than 200 nm, even more preferably less than 100 nm according to the use of a X-ray microscopy, for example, Xradia 810 Ultra 3D X-ray Microscope commercialized by Zeiss or which may be determined via removal of a micro-slice of the water-absorbing polymer particles (via a ultramicrotome) which is then subjected to a cryo-TEM methods, known in the art or by the use of the dynamic light scattering test method.

The dynamic light scattering test method is described in the article: Karpovich, A et al, "Determination of dimensions of exfoliating materials in aqueous suspensions", MethodsX, 2016, 3, 19-24. NMR relaxometry test method may also be used and is described in the same article above.

The clay platelets and the surface and/or edge-modified clay platelets in a carrier liquid may have a weight average largest particle size dimension (length) of at least 5 nm, preferably of at least 10 nm, more preferably of at least 20 nm according to the use of a X-ray microscopy, for example, Xradia 810 Ultra 3D X-ray Microscope commercialized by Zeiss, or which may be determined via removal of a micro-slice of the water-absorbing polymer particles (via a ultra-microtome) which is then subjected to a cryo-TEM methods, known in the art or by the use of the dynamic light scattering test method.

When the clay platelets have a large size dimension, it may be beneficial to break the larger size clay platelets by using an ultrasonic treatment before assessing their weight average largest particle size dimension as described above.

The clay platelets and the surface and/or edge-modified clay platelets in a carrier liquid may have an aspect ratio of less than 3000, preferably less than 1000, more preferably less than 300. The aspect ratio of clay platelets and the surface and/or edge-modified clay platelets in a carrier liquid is generally more than 5, preferably between 10 to 100, preferably between 10 to 50, more preferably between 10 to 30 and even more preferably 10 to 20.

The aspect ratio of clay platelet is the ratio of the largest dimension and the lowest dimension, orthogonal to it, of the clay platelet.

In the water-absorbing polymer particles, the clay platelets may be present as individual platelets or may be present as small aggregates of, for example, 2 to 5 clay platelets which may be determined via removal of a micro-slice of the water-absorbing polymer particles (via a ultramicrotome) which is then subjected to a cryo-TEM methods, known in the art or by the use of the dynamic light scattering test method.

The clay may be purified before surface-modification and/or edge-modification, e.g. to remove metals etc., by methods known in the art. For example, the clay to be modified may be a di-octahedral or tri-octahedral clay.

The surface and/or edge modification of the clay platelets may be done prior to adding the polymerizable monomers and the crosslinkers or simultaneously with adding of the polymerizable monomers and the crosslinkers. To obtain the surface and/or edge-modified clay platelets, the clay platelets may be dispersed in a carrier liquid that comprises the surface and/or edge modification compound(s), and/or the clay platelets may be dispersed in a carrier liquid, and the modification compound(s) may then be added to the dispersion, optionally also as solution or dispersion.

The ratio of clay platelets to surface and/or edge modification compound may be within the range of 1:1 to 100:1 (by weight, based on the weight of dry clay platelets and dry edge and/or surface modification compound(s)).

In the following, the surface and/or edge modification compounds are described as they are before addition to the clay platelets.

Edge Modification Compound(s)

When modifying the edges of the clay platelets, the exchangeable cations of the clay platelet edges may be replaced by the edge modification compound(s). Then, typically, the point of zero charge of the clay platelet edges is either shifted to a lower pH value, or the edge charge is made pH-independently neutral or pH-independently negative.

In addition, or alternatively, the edge modification compound may be a compound, which hinders and reduces aggregation of clay platelets.

The edge modification compound(s) may consist of one or more phosphorylation compounds. The phosphorylation compound(s) may be selected from the group consisting of: phosphate salts and/or derivatives thereof and/or acids forms thereof condensed phosphate salts, and/or derivatives thereof and/or acids forms thereof; phosponic acid, derivatives thereof and salts thereof and combinations thereof. For example, sodium pyrophosphate decahydrate may be suitably used. Organo-phosphor derivatives may also be useful.

The edge modification compound(s) may consist of one or more silanization compounds (also referred to as: silane compound).

The silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, N-Alkyls, Alkenes, alkenyls; and b) Alkoxy, hydrogen, toluenesulfonyl, sulfonyl containing moieties, chloride, halide; and c) hydroxy, carboxy-containing moieties, epoxy-containing moieties, provided that at least one moieties are selected from the subgroup b) or subgroup c) and that not more than three moieties are selected from said subgroup a).

Preferably, the silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, N-Alkyls, Alkenes, alkenyls; and b) Alkoxy, hydrogen, toluenesulfonyl, sulfonyl containing moieties, chloride, halide; and c) hydroxy, carboxy-containing moieties, epoxy-containing moieties, provided that at least from one to three moieties are selected from the subgroup a) and that at least one moieties are selected from the subgroup b) or subgroup c).

It may be beneficial that at least one of said moieties $R^{I}$, $R^{II}$, $R^{III}$, $R^{IV}$ is a moiety that is suitable to bond to the polymerizable monomer or polymerizable oligomer. For example, at least one of said moieties is an unsaturated moiety, such as vinyl. Preferably, the edge modification compound(s) is a silanization compound such as 7-Octenyldimethylmethoxysilane.

The edge modification compound(s) may consist of one or more fluorination compounds. Preferably, the edge modification compound(s) include fluoride salt. Preferably, the counterion M is a mono-valent counterion, such as sodium or ammonium.

The edge modification compound(s) may be a compound that sterically hinders from the aggregation of said platelet edges in order to reduce the risk of aggregation of the clay platelets in the solution, in addition to modifying the charge of the edges of the clay.

The edge modification compound(s) may have at least one moiety of at least 10 angstrom (A) or of at least 15 angstrom, or of at least 20 angstrom. Preferably the edge modification compound(s) have at least a moiety with a carbon chain of at least 6 carbon atoms, or at least 9 carbon atoms or at least 12 carbon atoms.

Other compounds to modify the edges of the clay platelet include epoxides. For example polyether clay platelets can be formed.

The edge-modification compound, in particular those described above as phosphorization, silanization or fluorination compounds, may have a further moiety or moieties that can ionically or covalently bind to the monomer or oligomer, or to the polymer formed; for example, the edge modification compound may have one or more unsaturated moieties (e.g. with C=C group), and/or one or more moieties that can form an ester or amide bond with the carboxyl group of the monomer, oligomer or polymer thereof, such as an oligo-ether or polyether moiety. Then, the edge modification compound not only binds to the edge of the clay platelet, but the compound(s) can also ionically or covalently bind to the polymers.

The clay platelets may not only be edge-modified to ensure homogeneous dispersion (and hence homogeneous incorporation in the crosslinked polymers network, after polymerization), but the edge modification may further serve to strongly bind the clay platelets to the crosslinked polymers network, e.g. covalently or ionically.

Surface Modification Compound(s)

The surface modification compound(s) may be a compound that has a cationic moiety (and/or: cationic at the pH of the liquid herein and reaction herein), that can bind to the negatively charged basal surface of the clay platelet. The surface modified clay may have surface(s) that are neutral (at the pH of the carrier liquid).

The surface modification compound(s) may comprise an alkylated nitrogen moiety, or alkoxylated nitrogen moiety, including for example linear, branched or cyclic amino-, ammonium-compounds. A majority of the moieties may be cationic at the pH of the reaction liquid/reaction.

The surface modification compound(s) may have one or more moieties selected from amines or imines, including derivatives thereof, such as diamines or diimines and/or ethylene or poly- or oligo-ethylene derivatives thereof, including hexamethylene diamine and derivatives thereof, ethylendiamine and derivatives thereof, oligo-alkyleneimine and derivatives thereof, such as linear or branched polyethyleneimine, olig-etheramines and derivatives thereof, linear or branched amides, or mixtures thereof.

The surface modification compound(s) may have an acryl amide moiety. The surface modification compound(s) may have a urethane moiety (bond by hydrogen bonding to the negative basal surface) or further modifications thereof. Preferably, the surface modification compound(s) may have a cationically modified urethane moiety.

Especially preferred are moieties selected from linear or branched polyethyleneimine, hexamethylene diamine or ethylendiamine, or derivatives of any of these, or mixtures thereof.

The surface modification compound(s) may also be a cationically modified oligo- or poly-saccharides, or derivative thereof.

In addition, the surface modification compound(s) may have one or more further moiety that is or are hydrophilic. This can aid dispersion of the surface-modified clay in the reaction liquid and/or can further enhance the hydrophilicity, and hence affinity for hydrophilic fluids (e.g. urine, blood, saline water), of the surface-coated water-absorbing polymer particles. This may for example be anionic moiety, or —OH. Preferably, the surface modification compound(s) has at least one moiety that is an alkoxylated moiety, carboxylated moiety, or sulfonated moiety, or sulfated moiety, to further improve hydrophilicity.

The surface modification compound(s) may be such that, when chemically bound (for example electrostatic bond) to the clay platelet surfaces, they introduce a sterically hindering moiety (s), which hinders and hence reduces aggregation of clay platelets. Hence, the surface modification compound (s) may have a moiety that is sterically hindering. Preferably, the surface modification compound(s) has one or more moieties that can provide sterical hindrance, having at least 6 carbon atoms, and/or a length of at least 10 angstrom, or at least 15 angstrom. Preferably, the surface modification compound(s) has an oligomer chain moiety.

For example, the surface modification compound(s) may have oligo-alkyleneoxide (AO) moiety, such as a oligo-ethyleneoxide (EO) moiety, with an average number of AO (e.g. EO)-repeating units of at least 2 or at least 5 or at least 10, and up to 100, or up to 60 or up to 40. Preferably, the surface modification compound(s) has at least a moiety that is an oligo-ethoxylate with a number of 2 to 40 repeating units.

The surface modification compound(s), in particular those with a cationic group as described above, may have a further moiety or moieties that can ionically or covalently bind to the monomer or oligomer, or to the polymer formed thereby; for example, the surface modification compound may have one or more unsaturated moieties (e.g. with C=C group), and/or one or more moieties that can form an ester or amide bond with the carboxyl group of the monomer, oligomer or polymer thereof, such as an oligo-ether or polyether moiety. Then, the surface modification compound not only binds to the surface of the clay platelet, but the compound(s) can also ionically or covalently bind to the polymers. Thus, the clay platelets are not only surface-modified to ensure homogeneous dispersion (and hence homogeneous incorporation in the final polymers, after polymerization), but the surface modification further serves to strongly bind to the polymers, e.g. covalently or ionically. The surface modification compound described herein above, e.g. with a cationic group, may for example comprise a polymerizable moiety, such as an alkylene, e.g. ethylene; and/or the unsaturated moiety may for example be an ester of acrylic acid, and/or an alkylated derivatives of acrylic acid, such as methacrylic acid.

It may be useful to apply during the surface and/or edge modification step and/or after the surface and/or edge modification step, an ultrasonic treatment step, and/or mixing step; preferred is the application of (e.g. high) shear mixing. For example, a Y-Tron mixer can be used. The exfoliation of the clay platelet may also be affected by use of high-shear mixers, (such as CB Loedige mixers, Schugi mixers, Littleford mixers, Drais mixers). The tip speed of any such mixers may for example be from at least 20 ms$^{-1}$, or at least 30 ms$^{-1}$ to for example 45 or 40 or 35 ms$^{-1}$.

The surface and/or edge modification of the clay platelets may be done in any liquid. It may for example be done in water. Alternatively, the surface and/or edge modification may be done in the absence of water, e.g. preferably in an anhydrous liquid, e.g. anhydrous liquid with a dielectric constant larger than 40 preferentially more than 50, for example propylene carbonate or ethylene carbonate. Preferred may be that the liquid phase comprises at least 80% by weight of water, preferably at least 90% or even 100% by weight of water.

Preferably, the surface and/or edge modification compound(s) modify the clay platelet prior to mixing with the polymerizable monomers and the crosslinkers. It may be preferred to modify the clay platelet's surfaces and/or edge, and then to wash the resulting modified clay platelet, and/or filtrate and or/submit to dialysis the modified clay platelet, prior to mixing with the polymerizable monomers and the crosslinkers.

Polymerization

The polymerizable compounds, i.e. polymerizable monomers, may be in the form of a dispersion or a solution. Preferably, the inorganic solid particles are in the form of a dispersion. Any combination of a dispersion or solution in a carrier liquid of polymerizable compounds, and separately, a dispersion of inorganic solid particles in a carrier liquid is herein referred to as "polymerizable solution".

The polymerizable compounds, e.g. polymerizable monomers, may be used herein as a solution or dispersion thereof in a carrier liquid, at a level of at least 1% by weight to 90% by weight, preferably from 10% by weight to 60% by weight. The carrier liquid is preferably an aqueous liquid.

The polymerizable solution may comprise polymerizable monomers, crosslinkers and inorganic solid particles. For example, the polymerizable solution may comprise homogeneously dispersed clay platelets with opposing basal platelet surfaces and platelet edges, polymerizable monomers and crosslinkers.

The polymerizable solution may be polymerizable by any type of polymerization reaction, by use of a polymerization initiator system that is activated, to initiate the polymerization. The polymerization initiator system may be activated by applying heat and/or radiation. After the polymerization, water-absorbing polymer particles are obtained.

The polymerizable solution may comprise from 0.1 to 10 wt % of inorganic solid particles, from 5 to 95 wt. % of water; from 5 to 95 wt. % of polymerizable monomers, from 0.001 to 10 wt. % of crosslinker, optionally a dispersing aid, and from 0.001 to 5 wt. % of polymerization initiator to start the polymerization.

The polymerizable solution may comprise from 0.1 to 10 wt % of modified clay platelet, from 5 to 95 wt. % of water; from 5 to 95 wt. % of polymerizable monomers, from 0.001 to 10 wt. % of organic crosslinker, optionally a dispersing aid, and from 0.001 to 5 wt. % of polymerization initiator to start the polymerization.

Method for Making Water-Absorbing Polymer Particles—Formula

The average closest distance between two neighboring crosslinkers ($R_{XL}$ in cm) in a water-absorbing polymer particle for a specific X-load of the water-absorbing polymer particle is calculated via the formula below:

$$Rxl = \left( \frac{\left( \frac{1}{rho\_dry} + \frac{x\_L}{rho\_liq} \right)}{N_A \cdot \sum_i \frac{w\_xl_i}{Mr\_CXL_i}} \right)^{\frac{1}{3}} \quad (I)$$

with x_L being the amount of liquid absorbed in the water-absorbing polymer particle in $g_{liq}/g_{water\text{-}absorbing\ polymer\ particle}$, rho_liq being the density at room temperature of the fluid that swells the water-absorbing polymer particle (generally saline of 0.9% w NaCl) in g/cm$^3$, rho_dry being the true density of the dry water-absorbing polymer particle in g/cm$^3$, Mr_CXL being the molar mass of the crosslinkers in g/mol, w_xl being the weight ratio of crosslinkers in dry water-absorbing polymer particle, $N_A$ being the Avogadro's number in mol$^{-1}$.

The formula above has been obtained as follows:

The average closest distance between two neighboring crosslinkers (Rxl in cm) in a water-absorbing polymer particle for a specific X-load of the water-absorbing polymer particle may be calculated via the formula below:

$$Rxl = \left( \frac{V\_gel}{Nxl} \right)^{1/3} \quad (II)$$

with V_gel being the volume of the gel at given X-load in cm$^3$, and $N_{xl}$ being the number of all crosslinkers in the cubic gel volume (V_gel) and as such it is the sum of all crosslinkers present in the cubic gel volume.

When more than one crosslinker types is present in the cubic gel volume, $N_{xl}$ corresponds to $\Sigma_i Nxl_i$.

The underlying assumption is that crosslinkers are uniformly distributed in space in a cubic gel volume (V_gel).

The number of all crosslinkers in the cubic gel volume ($N_{xl}$) may be calculated via the formula below:

$$Nxl = n\_xl N\_A \quad (III)$$

with N_A being the Avogadro's number in mol$^{-1}$, and n_xl being the moles of crosslinkers in mol and may be calculated via the formula below:

$$n\_xl = \frac{m\_xl}{Mr\_CXL} \quad (IV)$$

having Mr_CXL being the molar mass of the crosslinkers in g/mol, and m_xl is the mass of crosslinkers in g and may be calculated via the formula below:

$$w\_xl = \frac{m\_xl}{m\ dry} \quad (V)$$

so $$m\_xl = w\_xl m\_dry \quad (Va)$$

with w_xl being the weight ratio of crosslinkers in dry water-absorbing polymer particle, and m_dry being the mass of dry water-absorbing polymer particle in g.

Therefore, by substituting formula (IV) and (Va) into formula (III), the number of all crosslinkers in the cubic gel volume ($N_{xl}$) may be calculated via the formula below:

$$Nxl = \frac{w\_xl m\_dry N\_A}{Mr\_CXL} \quad (VI)$$

V_gel being the approximation of the gel volume as sum of the volume of the dry water-absorbing polymer particle (V_dry) and of the volume of the absorbed liquid (V_liq), i.e. assuming that liquid is linearly absorbed during swelling of the water-absorbing polymer particle, and is calculated via the equation below:

$$V\_gel = V\_dry + V\_liq \quad (VII)$$

With $$V\_dry = \frac{m\_dry}{rho\ dry} \quad (VIII)$$

having m_dry being the mass of dry water-absorbing polymer particle in g, rho_dry being the true density of the dry water-absorbing polymer particle in g/cm$^3$, and $$V\_liq = \frac{m\_liq}{rho\_liq} \quad (IX)$$

having m_liq being the mass of swelling liquid in g, and rho_liq being the density at room temperature of the fluid that swells the water-absorbing polymer particle (generally saline of 0.9% w NaCl) in g/cm$^3$.

The amount of liquid absorbed in the water-absorbing polymer particle (in g liq/g dry water-absorbing polymer particle) (x_L) is calculated via the formula below:

$$x\_L = \frac{m\_liq}{m\_dry} \tag{X}$$

so $$m\_liq = x\_L \cdot m\_dry \tag{Xa}$$

With m_dry being the mass of dry water-absorbing polymer particle in g, and m_liq being the mass of swelling liquid in g.

The X-load of the water-absorbing polymer particle is the amount of liquid absorbed by the water-absorbing polymer particles.

Therefore, by substituting formula (Xa) into formula (IX) and into formula (VII), and substituting formula (VIII) into formula (VII) and then both formula (VII) and (VI) into formula (II), we obtain the average closest distance between two neighboring crosslinkers (Rxl in cm) in a water-absorbing polymer particle for a specific X-load of the water-absorbing polymer particle calculated via the formula below:

$$Rxl = \left( \frac{\left( \frac{1}{rho\_dry} + \frac{x\_L}{rho\_liq} \right)}{N_A \cdot \frac{w\_xl}{Mr\_CXL}} \right)^{\frac{1}{3}} \tag{XI}$$

with x_L being the amount of liquid absorbed in the water-absorbing polymer particle in $g_{liq}/g_{water\text{-}absorbing\ polymer\ particle}$, rho_liq being the density at room temperature of the fluid that swells the water-absorbing polymer particle (generally saline of 0.9% w NaCl) in g/cm$^3$, rho_dry being the true density of the dry water-absorbing polymer particle in g/cm$^3$, Mr_CXL being the molar mass of the crosslinkers in g/mol, w_xl being the weight ratio of crosslinkers in dry water-absorbing polymer particle, $N_A$ being the Avogadro's number in mol$^{-1}$.

When more than one crosslinkers is used, the average closest distance between two neighboring crosslinkers (Rxl in cm) in a water-absorbing polymer particle for a specific X-load of the water-absorbing polymer particle is calculated via the formula below:

$$Rxl = \left( \frac{\left( \frac{1}{rho\_dry} + \frac{x\_L}{rho\_liq} \right)}{N_A \cdot \sum_i \frac{w\_xl_i}{Mr\_CXL_i}} \right)^{\frac{1}{3}} \tag{I}$$

Depending on the X-load of the water-absorbing polymer particle, the average closest distance between two neighboring crosslinkers ($R_{XL}$) in the water-absorbing polymer particle varies.

The X-load of the water-absorbing polymer particle may be for example 0 g/g, i.e. corresponding to the dry state of the water-absorbing polymer particle, 10 g/g, 20 g/g or 30 g/g.

The average closest distance between two neighboring crosslinkers ($R_{XL}$) in the water-absorbing polymer particle at 20 g/g X-load of the water-absorbing polymer particle obtained via the formula above is at least as high as an average size of the inorganic solid particles or higher than an average size of the inorganic solid particles.

Therefore, the inorganic solid particles present an average range of size that can fit the average closest distance between two neighboring crosslinkers ($R_{XL}$) in the water-absorbing polymer particle at 20 g/g X-load of the water-absorbing polymer particle.

The average range of size of the inorganic solid particles may be determined by measuring the diameter distribution of the inorganic solid particles by static Dynamic Light Scattering test method.

The dynamic light scattering test method is described in the article: Karpovich, A et al, "Determination of dimensions of exfoliating materials in aqueous suspensions", MethodsX, 2016, 3, 19-24. NMR relaxometry test method may also be used and is described in the same article above.

In particular, for inorganic solid particles with a lateral size over 100 nm, the most appropriate test method may be the static and dynamic light scattering test method in aqueous suspension as described in the article of Allen, T; Particle Size Measurement, Volume 1: Powder sampling and particle size measurement, 1997.

For inorganic solid particles with a lateral size below 100 nm, the most appropriate test method may be the Atomic Force Microscopy (AFM) test method which is described in the article of Cadene et al, Study of individual Na-montmorillonite particle size, morphology, and aparante charge, Journal of Colloid and Interface Science, 2005, 285, 719-730 and in Balnois et al, Langmuir 2003, 19, 6633.

"D10" is the particle size of the inorganic solid particles where 10% by weight of the particles are finer than this size according to the dynamic light scattering method described above.

"D50" is the particle size of the inorganic solid particles where 50% by weight of the particles are finer than this size according to the dynamic light scattering method described above.

"D90" is the particle size of the inorganic solid particles where 90% by weight of the particles are finer than this size according to the dynamic light scattering method described above.

"D84" is the particle size of the inorganic solid particles where 84% by weight of the particles are finer than this size according to the dynamic light scattering method described above.

Preferably, the average size of the inorganic solid particles is approximately equal to the value of the particle size D50 according to the dynamic light scattering method described above.

The average value of the particle size D50 may be 14 nm. So, the average size of the inorganic solid particles may be approximately equal to 14 nm according to the dynamic light scattering method described above.

Preferably, the inorganic solid particles of the invention have an average range of size that encloses the average size of the inorganic solid particles.

Preferably, the average range of size of the inorganic solid particles is from 3 to 100 nm according to the dynamic light scattering test method described above.

Preferably, the average range of size of the inorganic particles may be from 3 to 80 nm, more preferably from 3 to 70 nm and even more preferably from 3 to 50 nm according to the dynamic light scattering test method described above.

Preferably, the average range of size of the inorganic particles is from 10 to 20 nm according to the dynamic light scattering test method described above.

Alternatively, the average range of size of the inorganic solid particles may correspond to the range of values between D10 and D90.

Alternatively, the average range of size of the inorganic solid particles may correspond to the range of values between D10 and D84.

The average value of the particle size D84 may be 18.4 nm.

According to the formula described above, the average closest distance between two crosslinkers ($R_{XL}$) at 20 g/g X-load of the water-absorbing polymer particle is from 3 to 100 nm.

Preferably, the average distance between two crosslinkers ($R_{XL}$) at 20 g/g X-load of the water-absorbing polymer particle is from 3 to 80 nm, more preferably from 3 to 70 nm, more preferably from 3 to 50 nm, even more preferably from 5 to 20 nm according to formula (I) of the invention.

The concentration of crosslinkers ($C_{XL}$) in the water-absorbing polymer particle may be from 0.001 to 0.5 mol %, more preferably from 0.02 to 0.25 mol %, even more preferably from 0.05 to 0.15 mol %.

The concentration of inorganic solid particles in the water-absorbing polymer particle may be from 0.1 to 8% by weight compared to the total weight of the water absorbent polymer particle in dry state. Preferably, the concentration of inorganic solid particles in the water-absorbing polymer particle is from 0.5 to 3% by weight compared to the total weight of the water absorbent polymer particle in dry state.

The inorganic solid particles that can fit the average closest distance between two neighboring crosslinkers ($R_{XL}$) in the water-absorbing polymer particle at 20 g/g X-load of the water-absorbing polymer particle may act as barrier particles to the crosslinked polymer network such that the diffusion of the "extractables" outside of the crosslinked polymer network is limited but the influx of fluid through the crosslinked polymer network is not slowed down significantly by the inorganic solid particles.

The water-absorbing polymer particles obtained via the method of the invention may have a relatively low amount of "extractables".

The level of "extractables" in the water-absorbing polymer particles of the invention may be less than 15%, preferably less than 10% and more preferably less than 8% based on the total weight of the water-absorbing polymer particles. The water-absorbing polymer particles of the invention having a relatively low amount of "extractables" have good performance properties, especially in terms of effective capacity.

Properties of the Water-Absorbing Polymer Particles

The properties of water-absorbing polymer particles described herein may be characterized in various ways.

The Centrifuge Retention Capacity (CRC) measures the liquid absorbed by the water-absorbing polymer particles for free swelling in excess liquid.

The water-absorbing polymer particles of the invention may have a Centrifuge Retention Capacity (CRC) value of more than 25 g/g, preferably more than 26 g/g, more preferably more than 27 g/g as measured according to EDANA method NWSP 241.0.R2.

The water-absorbing polymer particles of the invention may have a Centrifuge Retention Capacity (CRC) value from 26 up to 50 g/g, or from 27 up to 40 g/g, or from 28 up to 35 g/g, as measured according to EDANA method NWSP 241.0.R2.

The CRC value does not reflect any external pressure apply on the water-absorbing polymer particles. The water-absorbing polymer particles having a high CRC value may be preferred since less water-absorbing polymer particles are needed to facilitate a required overall capacity for liquid absorption.

The Absorption Against Pressure (AAP) of water-absorbing polymer particles corresponds to the capability of the water-absorbing polymer particles to swell against external pressure. The term "external pressure" refers to the pressure applied on the absorbent core of an absorbent article by the wearer when he is seated for example or lay down.

The water-absorbing polymer particles may have a value of Absorption Against Pressure (AAP) of at least 22 g/g, preferably of at least 22.5 g/g, more preferably of at least 23 g/g, even more preferably of at least 23.5 g/g, still preferably of at least 24 g/g according to the Absorption Against Pressure Test Method.

The Absorption Against Pressure Test Method refers to the EDANA method WSP 442.2-02. However, contrary to the pressure specified in EDANA method WSP 442.2-02 (namely 0.3 psi), for the present invention the pressure applied on the sample is 0.7 psi.

The water-absorbing polymer particles may have a relatively high value of Absorption Against Pressure (AAP) in order to allow the water-absorbing polymer particles to swell properly against pressure.

Another parameter to define the properties of water-absorbing polymer particles may be used. It is called the Effective Capacity (EFFC). The Effective Capacity (EFFC) is calculated with the value of Centrifuge Retention Capacity (CRC) (EDANA method NWSP 241.0.R2) and with the value of Absorption Against Pressure (AAP) of the water-absorbing polymer particles. The Effective Capacity represents an average (arithmetic average) of the value of Centrifuge Retention Capacity (CRC) and of the value of Absorption Against Pressure (AAP) of the water-absorbing polymer particles.

The Effective Capacity (EFFC) is calculated via the formula below:

$$EFFC=(CRC+AAP)/2.$$

Preferably, the water-absorbing polymer particles have a value of Effective Capacity (EFFC) of at least 24.5 g/g, more preferably of at least 25 g/g, even more preferably of at least 25.5 g/g according to the EFFC test method.

Preferably, the water-absorbing polymer particles have a value of Effective Capacity (EFFC) between 25 g/g and 28 g/g, more preferably between 26 g/g and 28 g/g according to the EFFC test method.

The Absorption Against Pressure (AAP) of water-absorbing polymer particles is an important parameter to measure to the capability of the water-absorbing polymer particles to swell against external pressure. The Centrifuge Retention Capacity of water-absorbing polymer particles is another important parameter to measure the liquid absorbed by the water-absorbing polymer particles for free swelling in excess liquid. In order to have an overview of the situation depending on the pressure applied, an average value of Centrifuge Retention Capacity (CRC) and of the value of Absorption Against Pressure (AAP) of the water-absorbing polymer particles may be useful. That is why the Effective Capacity (EFFC) of the water-absorbing polymer particles is calculated.

The water-absorbing polymer particles may have a permeability at equilibrium expressed as UPM (Urine Permeability Measurement) value of more than 5 UPM, preferably more than 15 UPM, more preferably more than 30 UPM, more preferably more than 50 UPM, or even more preferably more than 70 UPM units according to the UPM test method, where 1 UPM unit is $1\times10^{-7}$ $(cm^3 \cdot s)/g$.

Preferably, the water-absorbing polymer particles have a value of UPM of at least 5 UPM units according to the UPM test method.

The UPM value is measured according to the UPM test method described herein. The UPM Test method typically measures the flow resistance of a pre-swollen water-absorbing polymer particles, i.e. the flow resistance is measured at equilibrium. Therefore, such water-absorbing polymer particles having a high UPM value exhibit a high permeability when a significant volume of the absorbent article is already wetted by the liquid exudates. These embodiments exhibit good absorption properties not only at the first gush but also at the subsequent gushes.

Absorbent Articles

A typical disposable absorbent article, in which the water-absorbing polymer particles of the present invention can be used, is placed against or in proximity to the body of the wearer to absorb and contain the various exudates discharged from the body and is represented in FIG. 1 to FIG. 5 in the form of a diaper 20.

In more details, FIG. 1 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbent articles.

Figure 2:
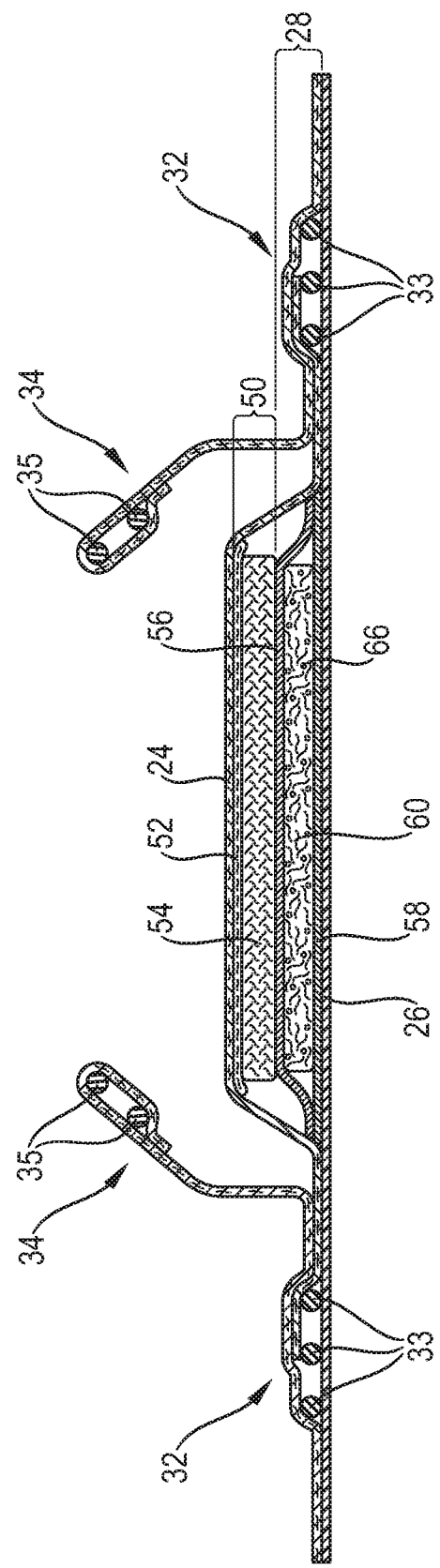
FIG. 2 is a transversal cross-section of the diaper of FIG. 1.

As shown in FIGS. 1 and 2, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as the water-absorbing polymer particles of the present invention 66 and/or cellulose fibers, as well as other absorbent and non-absorbent materials commonly used in absorbent articles (e.g. thermoplastic adhesives immobilizing the water-absorbing polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent core may comprise one or more substrate layer(s) (such as nonwoven webs or paper tissue), water-absorbing polymer particles disposed on the one or more substrate layers, and a thermoplastic composition typically disposed on the water-absorbing polymer particles. Typically the thermoplastic composition is a thermoplastic adhesive material. In one embodiment, the thermoplastic adhesive material forms a fibrous layer which is at least partially in contact with the water-absorbing polymer particles on the one or more substrate layers and partially in contact with the one or more substrate layers. Auxiliary adhesive might be deposited on the one or more substrate layers before application of the water-absorbing polymer particles for enhancing adhesion of the water-absorbing polymer particles and/or of the thermoplastic adhesive material to the respective substrate layer(s). The absorbent core may also include one or more cover layer(s) such that the water-absorbing polymer particles are comprised between the one or more substrate layer(s) and the one or more cover layer(s). The one or more substrate layer(s) and the cover layer(s) may comprise or consist of a nonwoven web. The absorbent core may further comprise odor control compounds.

The absorbent core may consist essentially of the one or more substrate layer(s), the water-absorbing polymer particles, the thermoplastic composition, optionally the auxiliary adhesive, optionally the cover layer(s), and optionally odor control compounds.

The absorbent core may also comprise a mixture of water-absorbing polymer particles and airfelt, which may be enwrapped within one or more substrate layers, such as nonwoven webs or paper tissue. Such absorbent cores may comprise from 30% to 95%, or from 50% to 95% of water-absorbing polymer particles by weight of the absorbent material and may comprise from 5% to 70%, or from 5% to 50% of airfelt by weight of the absorbent material (for these percentages, any enwrapping substrate layers are not considered as absorbent material). The absorbent core may also be free of airfelt and may comprise 100% of water-absorbing polymer particles by weight of the absorbent material.

The absorbent core may comprise mixtures of the water-absorbing polymer particles of the present invention and other water-absorbing polymer particles. For example, the absorbent core may comprise at least 70%, or at least 80%, or at least 90% or 100% of water-absorbing polymer particles by weight of the absorbent material, wherein the water-absorbing polymer particles comprise at least 10%, or at least 20% or at least 30% or at least 50% by weight of the water-absorbing polymer particles.

The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers.

The ADS may be free of water-absorbing polymer particles. The prior art discloses many types of acquisition-distribution systems, see for example WO2000/59430, WO95/10996, U.S. Pat. No. 5,700,254, WO02/067809. However, the water-absorbing polymer particles of the present invention may also be comprised by the ADS.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 $g/m^2$, in particular from 80 to 300 $g/m^2$.

The distribution layer may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13 to 15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 1 and 2. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 1 and 2 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Area(s) 29 Substantially Free of Absorbent Material and Channels 29'

Figure 3:
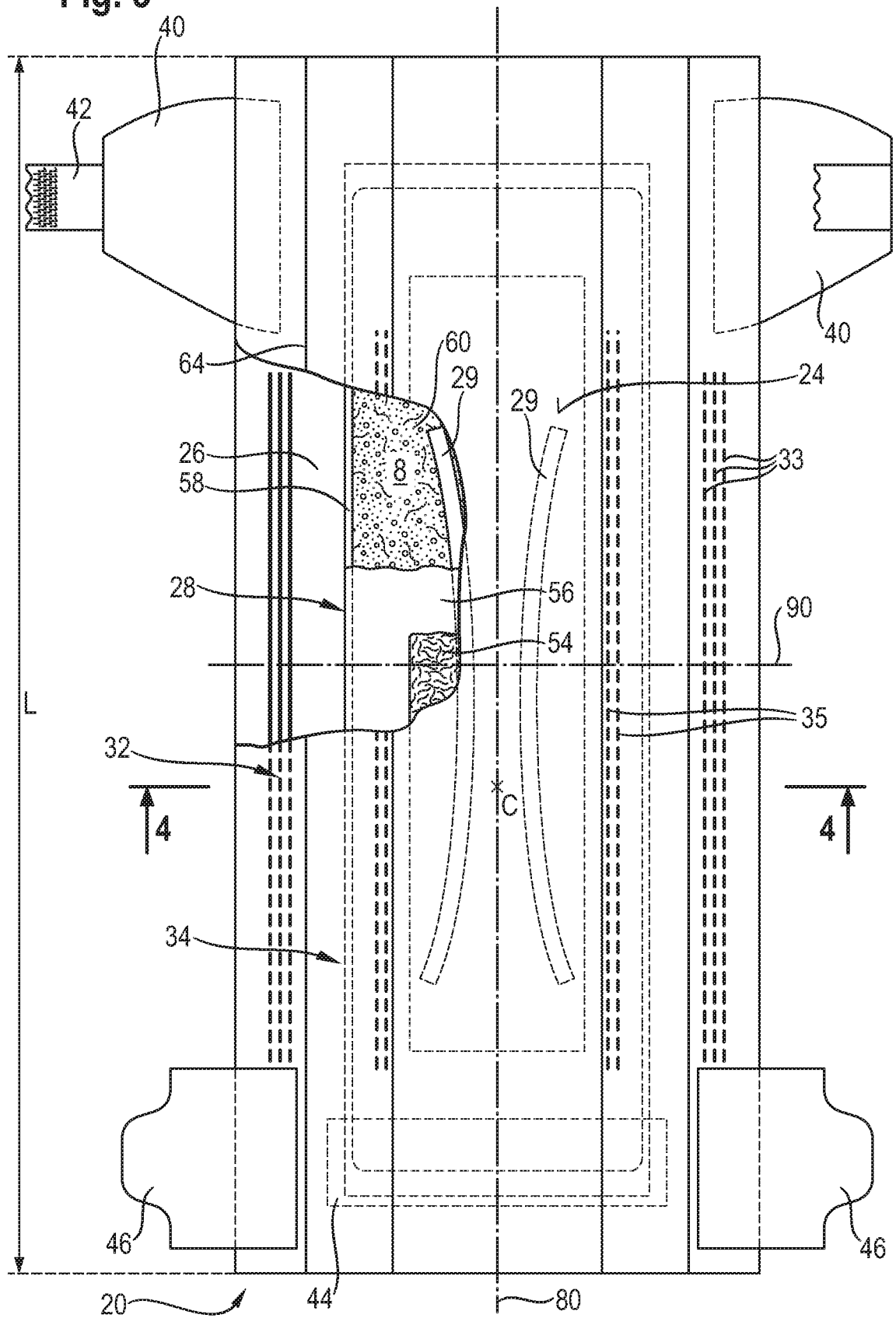
FIG. 3 is a top view of an exemplary absorbent article in the form of a diaper which may comprise the water-absorbing polymer particles of the present invention, with area(s) substantially free of absorbent material.

As shown in FIG. 3, the absorbent core 28 may comprise one or more area(s) 29 which is/are substantially free of absorbent material. By "substantially free" it is meant that in each of these areas the basis weight of the absorbent material is less than 25%, in particular less than 20%, less than 10%, of the average basis weight of the absorbent material in the rest of the core. In particular there can be no absorbent material in these areas. Minimal amount such as involuntary contaminations with absorbent material that may occur during the making process are not considered as absorbent material. The areas 29 are advantageously surrounded by the absorbent material, when seen in the plane of the core, which means that the area(s) 29 does not extend to any of the edge of the deposition area 8 of the absorbent material.

Figure 4:
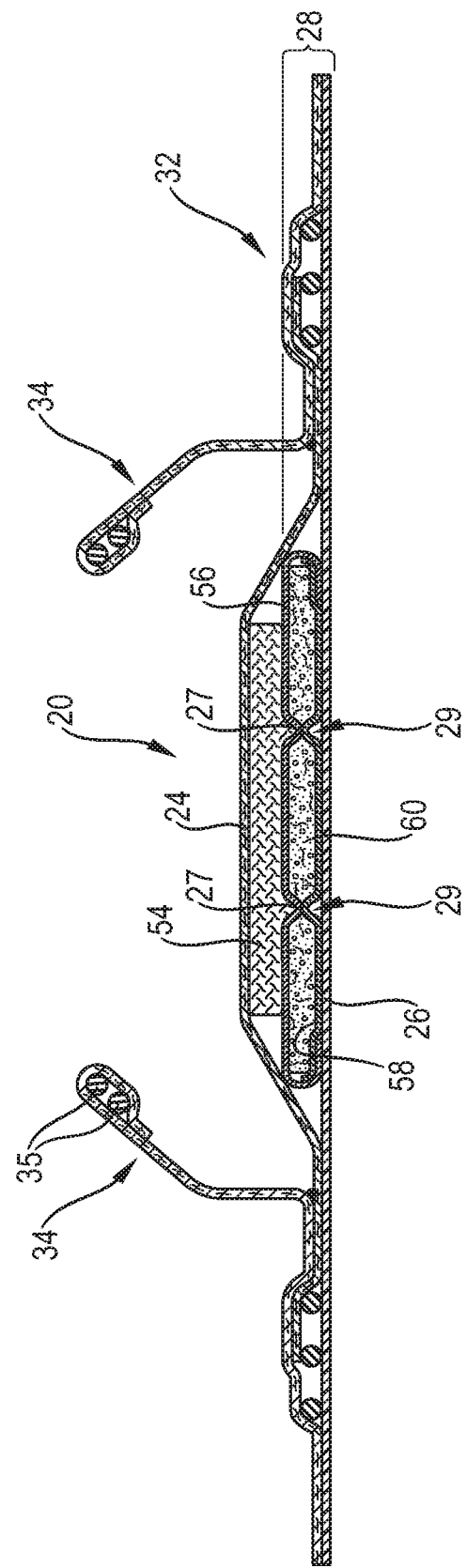
FIG. 4 is a transversal cross-section of the article of FIG. 3.
Figure 5:
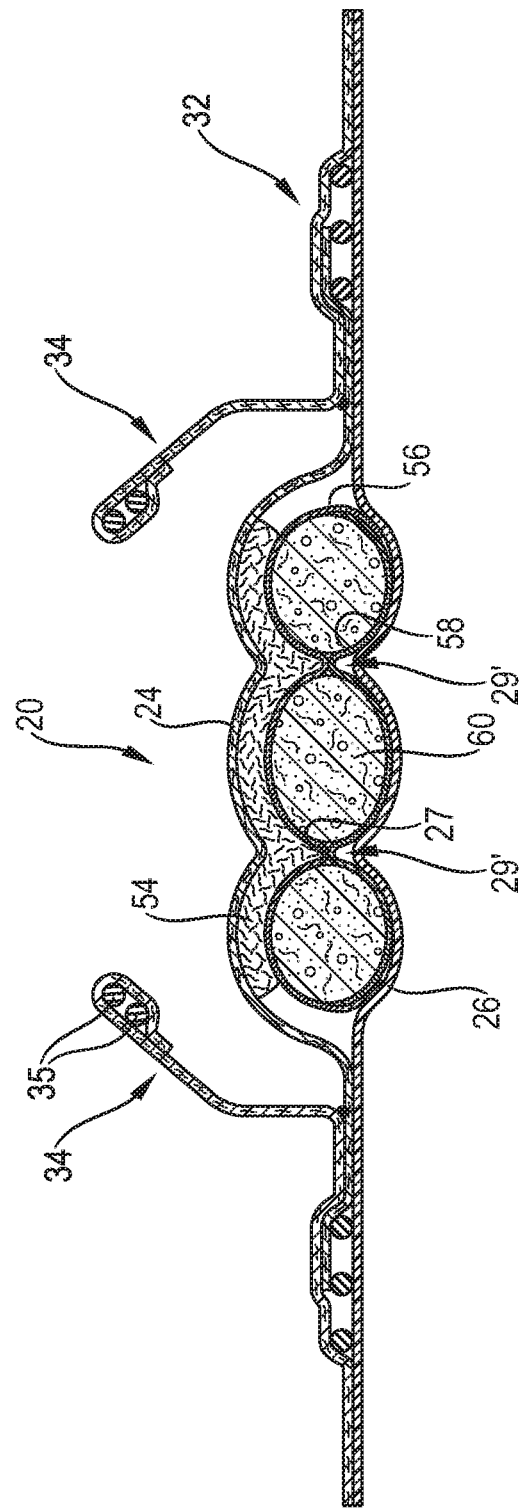
FIG. 5 is a transversal cross-section of the article taken at the same point as FIG. 4 where channels have formed in the core as a result of the diaper being loaded with fluid.

The upper core cover layer 56 is attached to the lower cover layer 58 by core wrap bond(s) 27 through these area(s) 29 substantially free of absorbent material. As shown in FIG. 4 and FIG. 5, when the absorbent material swells upon absorbing a liquid, the core wrap bond remains at least initially attached in the substantially material free area(s) 29. The absorbent material swells in the rest of the core when it absorbs a liquid, so that the core wrap forms one or more channel(s) 29' along the area(s) 29 substantially free of absorbent material comprising the core wrap bond 27. These channels 29' are three dimensional and can serve to distribute an insulting fluid along their length to a wider area of the core. This may provide a quicker fluid acquisition speed and a better utilization of the absorbent capacity of the core. The channels 29' can also provide a deformation of an overlying layer such as a fibrous layer 54 and provide corresponding ditches 29 in the overlying layer. It is not excluded that the absorbent core may comprise other area(s) substantially free of absorbent material but without a core wrap bond, but these non-bonded areas will typically not form a channel when wet.

The upper core cover layer 56 and the lower cover layer 58 may be attached together continuously along the area(s) 29 substantially free of absorbent material, but the core wrap bond 27 may also be discontinuous (intermittent) such as series of point bonds. Typically, an adhesive can be used to attach the top side to the bottom of the core wrap, but it is possible to bond via other known attachment means, such as pressure bonding, ultrasonic bonding or heat bonding or combination thereof. The attachment of the top side and bottom side of the core wrap may be provided by one or more adhesive material, in particular one or more layers of auxiliary glue and/or one or more layers of fibrous adhesive material, if present in the core, as indicated below. These glues may therefore serve the dual function of immobilizing the absorbent material and attach the top side and the bottom side of the core together.

The following examples of the shape and size of the areas 29 substantially free of absorbent material are not limiting. In general, the core wrap bond 27 may have the same outline but be slightly smaller than the areas 29 due to the tolerance required in some manufacturing process. The substantially material free area(s) 29 may be present within the crotch region of the article, in particular at least at the same longitudinal level as the crotch point C, as represented in FIG. 3 by the two longitudinally extending areas substantially free of absorbent material 29. The absorbent core 28 may also comprise more than two substantially absorbent material free area(s), for example at least 3, or at least 4 or at least 5 or at least 6. The absorbent core may comprise one or more pairs of areas substantially free of absorbent material symmetrically arranged relative to the longitudinal axis 80. Shorter area(s) substantially free of absorbent material may also be present, for example in the back region or the front region of the core, as seen for example in the Figures of WO2012/170778.

The area(s) 29 substantially free of absorbent material may extend substantially longitudinally, which means typically that each area extends more in the longitudinal direction than in the transverse direction, and typically at least twice as much in the longitudinal direction than in the transverse direction (as measured after projection on the respective axis). The area(s) 29 substantially free of absorbent material may have a length projected on the longitudinal axis 80 of the core that is at least 10% of the length of the absorbent core, in particular from 20% to 80%. It may be advantageous that at least some or all of the area(s) 29 are not completely or substantially completely transversely oriented channels in the core.

The area(s) 29 substantially free of absorbent material may be completely oriented longitudinally and parallel to the longitudinal axis but also may be curved. In particular some or all these area(s), in particular these area(s) present in the crotch region, may be concave towards the longitudinal axis 80, as for example represented in FIG. 3 for the pair of channels 29'. The radius of curvature may typically be at least equal (and preferably at least 1.5 or at least 2.0 times this average transverse dimension) to the average transverse dimension of the absorbent material deposition area 8; and also straight but under an angle of (e.g. from 5°) up to 30°, or for example up to 20°, or up to 10° with a line parallel to the longitudinal axis. The radius of curvature may be constant for a substantially absorbent material free area (s), or may vary along its length. This may also includes area(s) substantially free of absorbent material with an angle therein, provided said angle between two parts of a channel is at least 120°, preferably at least 150°; and in any of these cases, provided the longitudinal extension of the area is more than the transverse extension. These area(s) may also be branched, for example a central substantially material free area superposed with the longitudinal axis in the crotch region which branches towards the back and/or towards the front of the article.

In some embodiments, there is no area(s) substantially free of absorbent material that coincides with the longitudinal axis 80 of the core. When present as one ore symmetrical pair(s) relative to the longitudinal axis, the area(s) substantially free of absorbent material may be spaced apart from one another over their whole longitudinal dimension. The smallest spacing distance may be for example at least 5 mm, or at least 10 mm, or at least 16 mm.

Furthermore, in order to reduce the risk of fluid leakages, the area(s) substantially free of absorbent material may advantageously not extend up to any of the edges of the absorbent material deposition area 8, and are therefore surrounded by and fully encompassed within the absorbent material deposition area 8 of the core. Typically, the smallest distance between an area(s) substantially free of absorbent material and the closest edge of the absorbent material deposition area is at least 5 mm.

The area(s) substantially free of absorbent material may have a width Wc along at least part of its length which is at least 2 mm, or at least 3 mm or at least 4 mm, up to for example 20 mm, or 16 mm or 12 mm. The width Wc of the area(s) substantially free of absorbent material may be constant through substantially its whole length or may vary along its length.

The channels 29' in the absorbent core start forming when the absorbent material absorbs a liquid such as urine and starts swelling. As the core absorbs more liquid, the depressions within the absorbent core formed by channels will become deeper and more apparent to the eye and the touch. It is possible to create a sufficiently strong core wrap bond combined with a relatively low amount of water-absorbing polymer particles so that the channels remain permanent until complete saturation of the absorbent material. On the other hand, the core wrap bonds may in some cases also restrict the swelling of the absorbent material when the core is substantially loaded.

Initially, the core wrap bond(s) may be designed to be closed and to increase the pressure in the areas adjacent to the core wrap bond(s). At some point, the core wrap bond 27 may also be designed to open in a controlled manner when exposed to a large amount of fluid.

Test Methods

Urine Permeability Measurement (UPM) Test Method

Lab Conditions:

This test has to be performed in a climate conditioned room at standard conditions of 23° C.±2° C. temperature and 45%±10% relative humidity.

Urine Permeability Measurement System

This method determined the permeability of a swollen hydrogel layer 1318. The equipment used for this method is described below. This method is closely related to the SFC (Salt Flow Conductivity or Saline Flow Conductivity) test method of the prior art.

Figure 6:
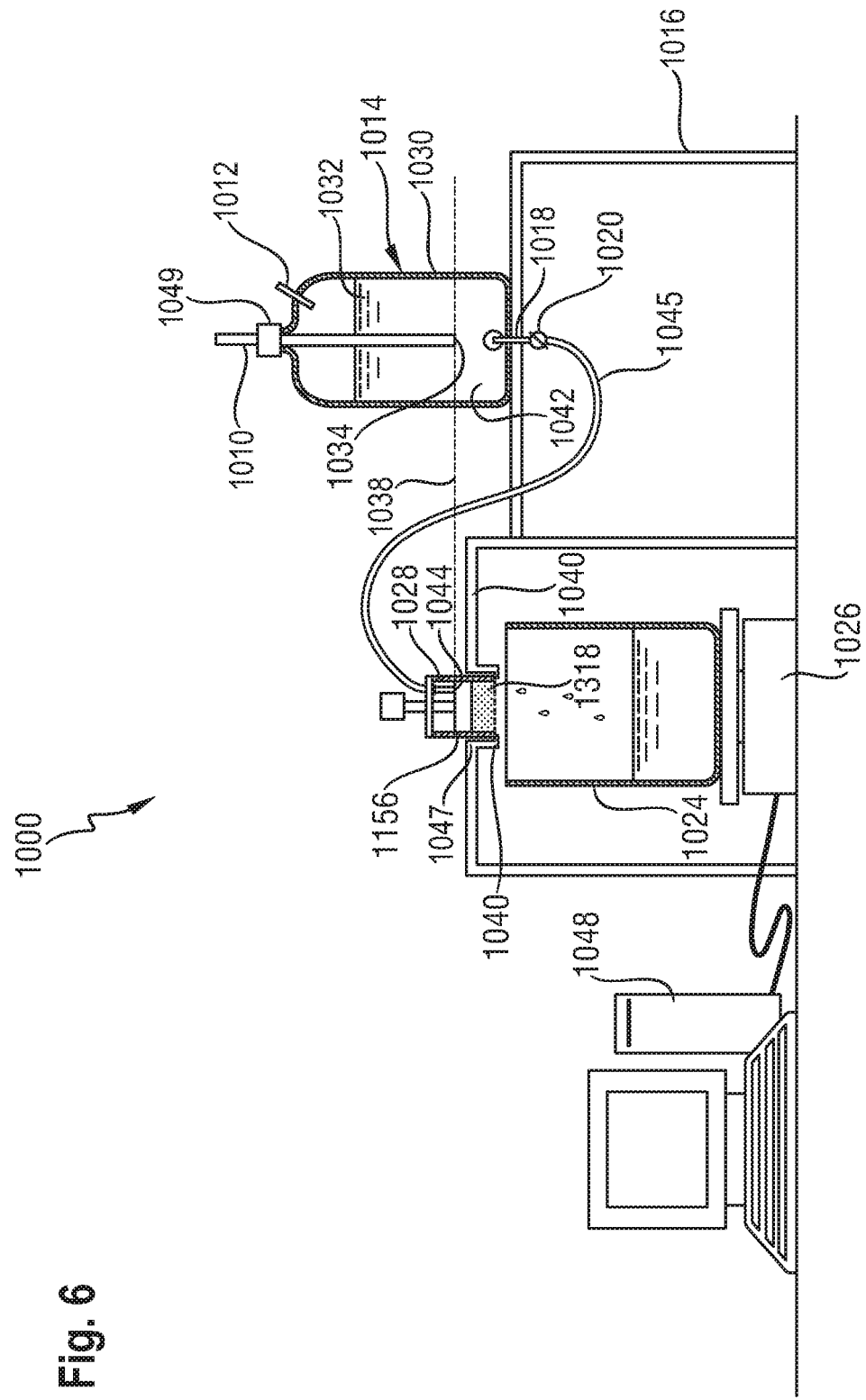
FIG. 6 is a partial cross-sectional side view of a suitable permeability measurement system for conducting the Urine Permeability Measurement Test.

FIG. 6 shows permeability measurement system 1000 set-up with the constant hydrostatic head reservoir 1014, open-ended tube for air admittance 1010, stoppered vent for refilling 1012, laboratory reck 1016, delivery tube 1018 with flexible tube 1045 with Tygon tube nozzle 1044, stopcock 1020, cover plate 1047 and supporting ring 1040, receiving vessel 1024, balance 1026 and piston/cylinder assembly 1028.

Figure 7:
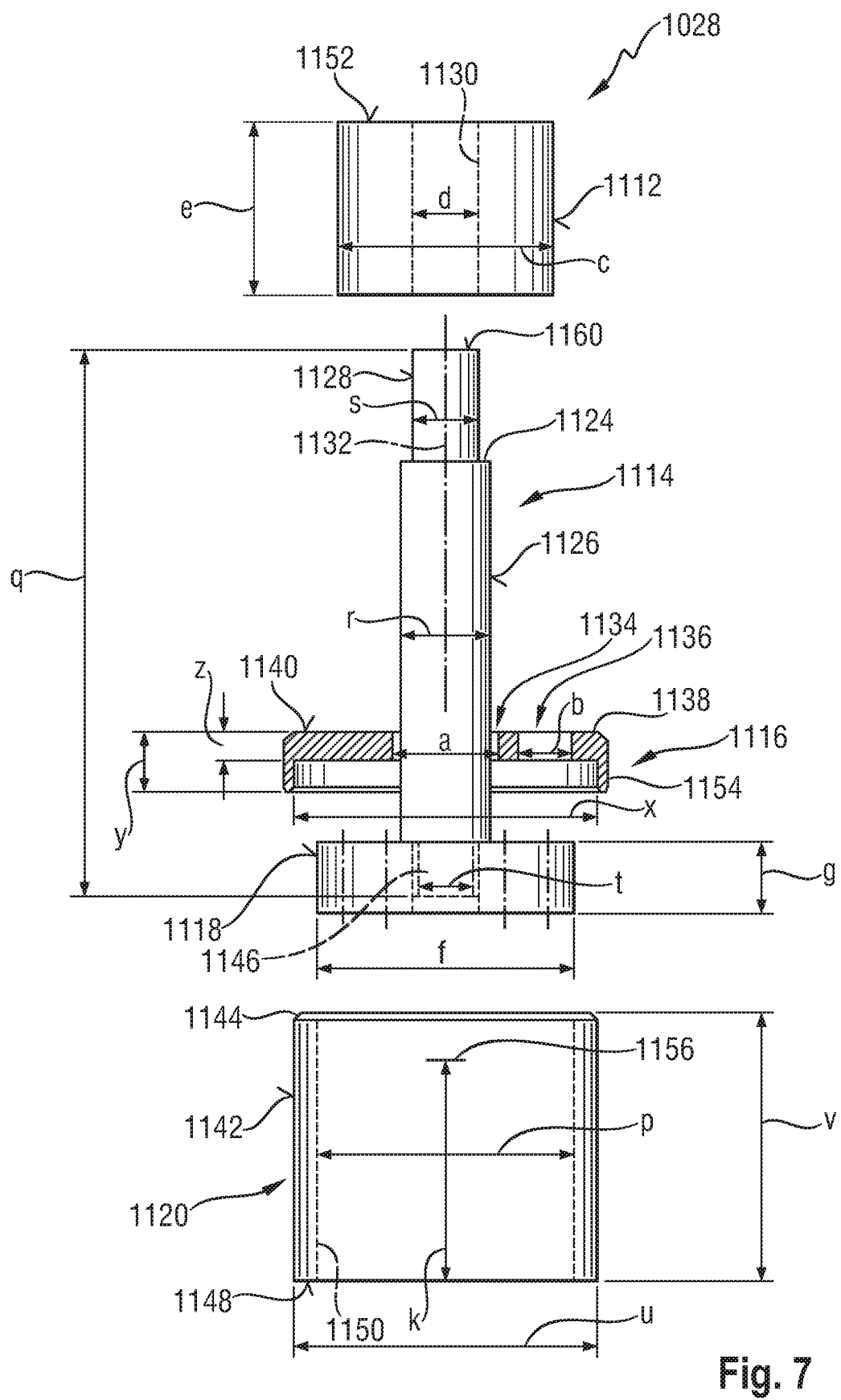
FIG. 7 is a cross-sectional side view of a piston/cylinder assembly for use in conducting the Urine Permeability Measurement Test.
Figure 8:
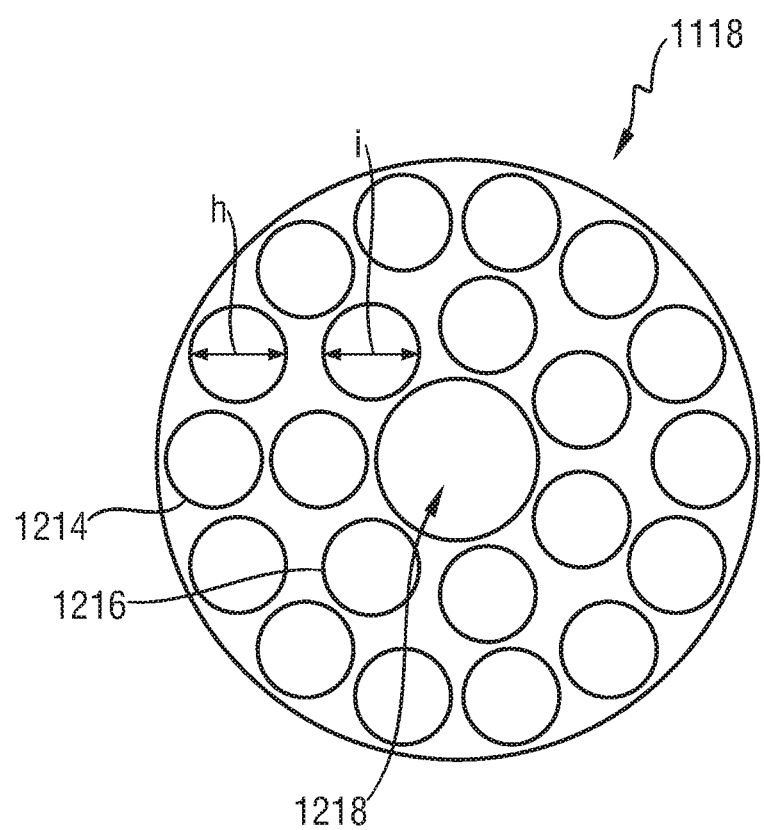
FIG. 8 is a top view of a piston head suitable for use in the piston/cylinder assembly shown in FIG. 7.

FIG. 7 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm$^2$) with inner cylinder walls 1150 which are smooth. The bottom 1148 of the cylinder 1120 is faced with a stainless-steel screen cloth (ISO 9044 Material 1.4401, mesh size 0.038 mm, wire diameter 0.025 mm) (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 22.15 (±0.02) mm. An upper portion 1128 of the piston shaft 1114 has a diameters of 15.8 mm, forming a shoulder 1124. A lower portion 1146 of the piston shaft 1114 has a diameter t of approximately ⅝ inch (15.9 mm) and is threaded to screw firmly into the center hole 1218 (see FIG. 8) of the piston head 1118. The piston head 1118 is perforated, made of transparent polycarbonate (e.g., Lexan®), and is also screened with a stretched stainless-steel screen cloth (ISO 9044 Material 1.4401, mesh size 0.038 mm, wire diameter 0.025 mm) (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the inner area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be repositioned with the same orientation relative to one another for each measurement.

The cylinder 1120 specification details are:
Outer diameter u of the Cylinder 1120: 70.35 mm (±0.05 mm)
Inner diameter p of the Cylinder 1120: 60.0 mm (±0.05 mm)
Height v of the Cylinder 1120: 60.5 mm. Cylinder height must not be lower than 55.0 mm!

The cylinder lid 1116 specification details are:
Outer diameter w of cylinder lid 1116: 76.05 mm (±0.05 mm)
Inner diameter x of cylinder lid 1116: 70.5 mm (±0.05 mm)
Thickness y of cylinder lid 1116 including lip 1154: 12.7 mm
Thickness z of cylinder lid 1116 without lip 1154: 6.35 mm
Diameter a of first lid opening 1134: 22.25 mm (±0.02 mm)
Diameter b of second lid opening 1136: 12.7 mm (±0.1 mm)
Distance between centers of first and second lid openings 1134 and 1136: 23.5 mm The weight 1112 specification details are:
Outer diameter c: 50.0 mm
Diameter d of center bore 1130: 16.0 mm
Height e: 39.0 mm The piston head 1118 specification details are:
Diameter f: 59.7 mm (±0.05 mm)
Height g: 16.5 mm. Piston head height must not be less than 15.0 mm.
Outer holes 1214 (14 total) with a 9.30 (±0.25) mm diameter h, outer holes 1214 equally spaced with centers being 23.9 mm from the center of center hole 1218.
Inner holes 1216 (7 total) with a 9.30 (±0.25) mm diameter i, inner holes 1216 equally spaced with centers being 13.4 mm from the center of center hole 1218.
Center hole 1218 has a diameter j of approximately ⅝ inches (15.9 mm) and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the cover plate 1047 and supporting ring 1040 (with circular inner opening of not less than 64 mm diameter) above the receiving vessel 1024.

The cover plate 1047 and supporting ring 1040 are parts as used in the equipment used for the method "K(t) Test Method (Dynamic Effective Permeability and Uptake Kinetics Measurement Test method)" as described in EP 2 535 027 A1 and is called "Zeitabhängiger Durchlässigkeitsprüfstand" or "Time Dependent Permeability Tester", Equipment No. 03-080578 and is commercially available at BRAUN GmbH, Frankfurter Str. 145, 61476 Kronberg, Germany. Upon request, detailed technical drawings are also available.

Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 connected to a flexible tube 1045 (e.g. Tygon tube, capable to connect nozzle and reservoir outlet) and to a Tygon tube nozzle 1044 (inner diameter at least 6.0 mm, length appr. 5.0 cm) for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of approximately 12 mm, but not less than 10.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery flexible tube 1045 is dimensioned (e.g. outer diameter 10 mm) to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar 1049. The constant hydrostatic head reservoir 1014 can be positioned on a laboratory reck 1016 at a suitable height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 2.6 g/sec for at least 10 minutes.

The piston/cylinder assembly 1028 is positioned on the supporting ring 1040 in the cover plate 1047 or suitable alternative rigid stand. The salt solution 1032 passing through the piston/cylinder assembly 1028 containing the swollen hydrogel layer 1318 is collected in a receiving vessel 1024, positioned below (but not in contact with) the piston/cylinder assembly 1028.

The receiving vessel 1024 is positioned on the balance 1026 which is accurate to at least 0.001 g. The digital output of the balance 1026 is connected to a computerized data acquisition system 1048.

Preparation of Reagents (not Illustrated)

Figure 9:
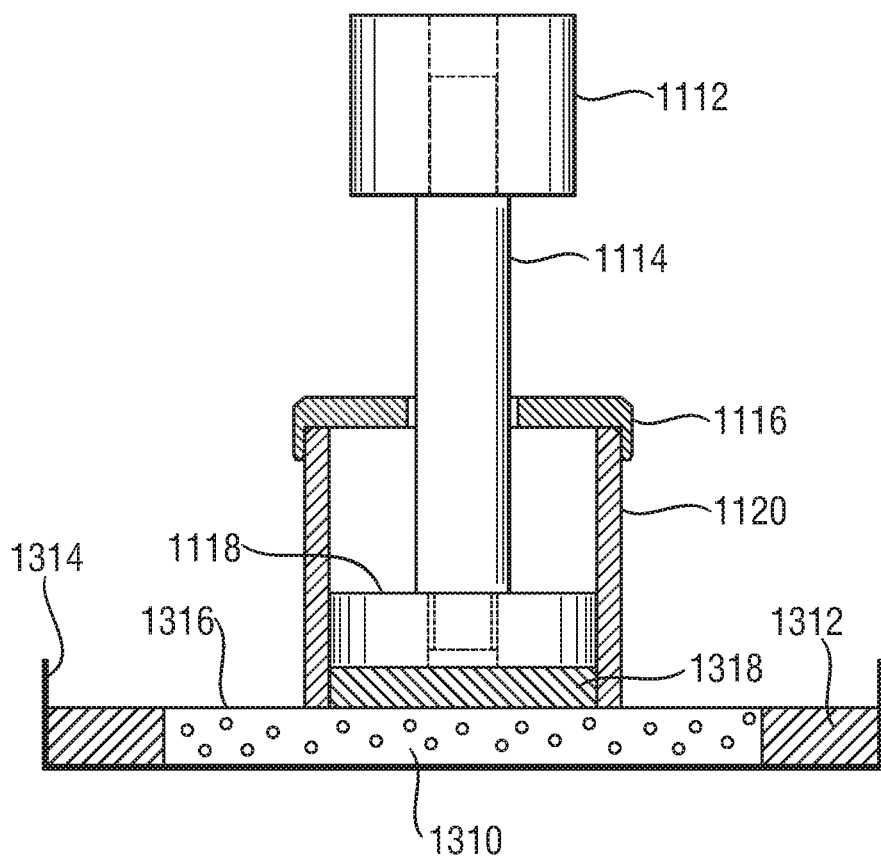
FIG. 9 is a cross-sectional side view of the piston/cylinder assembly of FIG. 7 placed on fritted disc for the swelling phase.

Jayco Synthetic Urine (JSU) 1312 (see FIG. 9) is used for a swelling phase (see UPM Procedure below) and 0.118 M Sodium Chloride (NaCl) Solution 1032 is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of Salts to Make 1 Liter of Jayco Synthetic Urine:
Potassium Chloride (KCl) 2.00 g
Sodium Sulfate (Na2SO4) 2.00 g
Ammonium dihydrogen phosphate (NH4H2PO4) 0.85 g
Ammonium phosphate, dibasic ((NH4)2HPO4) 0.15 g
Calcium chloride (CaCl2) 0.19 g—[or hydrated calcium chloride (CaCl2.2H2O) 0.25 g]
Magnesium chloride (MgCl2) 0.23 g—[or hydrated magnesium chloride (MgCl2.6H2O) 0.50 g]

To make the preparation faster, potassium chloride, sodium sulfate, ammonium dihydrogen phosphate, ammonium phosphate (dibasic) and magnesium chloride (or hydrated magnesium chloride) are combined and dissolved in the 80% of distilled water in the 1 L volumetric flask. Calcium chloride (or hydrated calcium chloride) is dissolved separately in approximately 50 ml distilled water (e.g. in a glass beaker) and the calcium chloride solution is transferred to the 1 L volumetric flask after the other salts are completely dissolved therein. Afterwards, distilled water is added to 1 L (1000 ml±0.4 ml) and the solution is stirred for a few minutes more. Jayco synthetic urine may be stored in a clean plastic container for 10 days. The solution should not be used if it becomes cloudy.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask (1000 ml±0.4 ml); and the flask is filled to volume with distilled water. A stir bar is added and the solution is mixed on a stirring plate until all the solids are dissolved.

The conductivity of the prepared Jayco solution must be in the range of appr. 7.48-7.72 mS/cm and of the prepared 0.118 M Sodium Chloride (NaCl) Solution in the range of appr. 12.34-12.66 mS/cm (e.g. measured via COND 70 INSTRUMENT without CELL, #50010522, equipped with Cell VPT51-01 C=0.1 from xs instruments or via LF 320/Set, #300243 equipped with TetraCon 325 from WTW or COND 330i, #02420059 equipped with TetraCon 325 from WTW). The surface tension of each of the solutions must be in the range of 71-75 mN/m (e.g. measured via tensiometer K100 from Kruess with Pt plate).

Test Preparation

Using a solid reference cylinder weight (not shown) (50 mm diameter; 128 mm height), a caliper gauge (not shown) (measurement range 25 mm, accurate to 0.01 mm, piston pressure max. 50 g; e.g. Mitutoyo Digimatic Height Gage) is set to read zero. This operation is conveniently performed on a smooth and level bench (not shown) of at least approximately 11.5 cm×15 cm. The piston/cylinder assembly 1028 without superabsorbent polymer particles is positioned under the caliper gauge (not shown) and a reading, L1, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system 1048. The cover plate 1047 with the supporting ring 1040 is positioned above the receiving vessel 1024.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method NWSP 230.0.82 (15) or via a Moisture Analyzer (HX204 from Mettler Toledo, drying temperature 130° C., starting superabsorber weight 3.0 g (±0.5 g), stop criterion 1 mg/140 s). If the moisture content of the superabsorbent polymer particles is greater than 3 wt %, then the superabsorbent polymer particles are dried to a moisture level of <3 wt %, e.g. in an oven at 105° C. for 3 h or e.g. at 120° C. for 2 h. Agglomerated superabsorbent polymer particles are dried if moisture level is greater than 5 wt %, e.g. in an oven at 105° C. for 3 h or e.g. at 120° C. for 2 h.

The empty cylinder 1120 is placed on a level benchtop 1046 (not shown) and the superabsorbent polymer particles are quantitatively transferred into the cylinder 1120. The superabsorbent polymer particles are evenly dispersed on the screen (not shown) attached to the bottom 1148 of the cylinder 1120 while rotating the cylinder 1120, e.g. aided by a (manual or electrical) turn table (e.g. petriturn-E or petriturn-M from Schuett). It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The weight 1112 is positioned on the upper portion 1128 of the piston shaft 1114 so that it rests on the shoulder 1124 such that the first and second linear index marks are aligned. The lid 1116 and piston shaft 1126 are then carefully rotated so as to align the third, fourth, fifth, and sixth linear index marks are then aligned with the first and the second linear index marks. The piston head 1118 (via the piston shaft 1114) is then gently lowered to rest on the dry superabsorbent polymer particles. Proper seating of the lid 1116 prevents binding and assures an even distribution of the weight on the hydrogel layer 1318.

Swelling Phase:

A fritted disc of at least 8 cm diameter (e.g. 8-9 cm diameter) and at least 5.0 mm thickness (e.g. 5-7 mm thickness) with porosity "coarse" or "extra coarse" (e.g. Chemglass Inc. #CG 201-51, coarse porosity; or e.g. Robu 1680 with porosity 0) 1310 is placed in a wide flat-bottomed Petri dish 1314 and JSU 1312 is added by pouring JSU 1312 onto the center of the fritted disc 1310 until JSU 1312 reaches the top surface 1316 of the fritted disc 1310. The JSU height must not exceed the height of the fritted disc 1310. It is important to avoid any air or gas bubbles entrapped in or underneath the fritted disc 1310.

The entire piston/cylinder assembly 1028 is lifted and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fritted disc 1310. After a period of 60 minutes, the piston/cylinder assembly 1028 is removed from the fritted disc 1310, taking care to ensure the hydrogel layer 1318 does not lose JSU 1312 or take in air during this procedure. The piston/cylinder assembly 1028 is placed under the caliper gauge (not shown) and a reading, L2, is recorded to the nearest 0.01 mm. If the reading changes with time, only the initial value is recorded. The thickness of the hydrogel layer 1318, L0 is determined from L2−L1 to the nearest 0.1 mm.

The piston/cylinder assembly 1028 is transferred to the supporting ring 1040 in the cover plate 1047. The constant hydrostatic head reservoir 1014 is positioned such that the delivery tube nozzle 1044 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer 1048 attached to the balance 1026, the quantity g (in g to accuracy of 0.001 g) of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation.

For each time period of 20 seconds (time $t_{(i-1)}$ to $t_i$) after the initial 60 seconds of the experiment, the respective flow rate $Fs_{(t)}$ (in g/s) and the respective mid-point of the time $t_{(1/2)t}$ (in s) is calculated according to the following formulas:

$$Fs_{(t)} = \frac{(g_{(i-1)} - g_{(i)})}{(t_{(i-1)} - t_{(i)})} \text{ and } t_{(1/2)t} = \frac{(t_{(i-1)} + t_{(i)})}{2} \tag{XII}$$

The flow rate $Fs_{(t)}$ of each time interval ($t_{(i-1)}$ to $t_i$) is plotted versus the mid-point of the time $t_{(1/2)t}$ of the time interval ($t_{(i-1)}$ to $t_i$). The intercept is calculated as Fs(t=0).

Calculation of the Intercept:

The intercept is calculated via a best-fit regression line, e.g. as following: the equation for the intercept of the regression line, a, is:

$$a = y_{AVG} - b \cdot x_{AVG} \tag{XIII}$$

where the slope, b, is calculated as:

$$b = \frac{\sum (x - x_{AVG}) \cdot (y - y_{AVG})}{\sum (x - x_{AVG})^2} \tag{XIV}$$

and where $X_{AVG}$ and $Y_{AVG}$ are the sample means AVERAGE of the known_x's and AVERAGE of the known_y's, respectively.

Calculation of Urine Permeability Measurement Q:

The intercept Fs(t=0) is used to calculate Q according to the following formula:

$$Q = \frac{F_s(t=0) \cdot L_0}{\rho \cdot A \cdot \Delta P} \tag{XV}$$

where the flow rate Fs(t=0) is given in g/s, $L_0$ is the initial thickness of the hydrogel layer 1318 in cm, $\rho$ is the density of the salt solution 1032 in $g/cm^3$ (e.g. 1.003 $g/cm^3$ at room temperature). A (from the equation above) is the area of the hydrogel layer 1318 in $cm^2$ (e.g. 28.27 $cm^2$), $\Delta P$ is the hydrostatic pressure in $dyne/cm^2$ (e.g. 4920 $dyne/cm^2$), and the Urine Permeability Measurement, Q, is in units of $cm^3$ sec/g. The average of three determinations should be reported.

TABLE 1

| Variable | Description | Unit |
|---|---|---|
| $g_i$ | Mass of salt solution 1032 flown through the swollen gel layer (recorded by the balance) at the time $t_i$ (accuracy 0.001 g) | g |
| $t_i$ | Time point (every 20 s) | s |
| $t_{(1/2)i'}$ | Mid-point of time for the respective time interval $t_{i-1}$ to $t_i$ | s |
| $Fs_t$ | Flow Rate at the time interval $t_{i-1}$ to $t_i$ | g/s |
| Fs (t = 0) | Intercept flow rate at t = 0 s from the plot of the flow rate Fs(t) vs. the mid-point of time $t_{(1/2)i'}$. | g/s |
| $L_0$ | Thickness of the swollen gel layer (swollen with JSU 1312) before the salt solution 1032 flows through the gel layer. | cm |
| ρ | Density of the salt solution 1032 (1.003 g/cm$^3$) | g/cm$^3$ |
| A | Area of the swollen gel layer (28.27 cm$^2$) | cm$^2$ |
| ΔP | Hydrostatic pressure across the gel layer (4920 dyne/cm$^2$) | dyne/cm$^2$ |
| Q | Urine Permeability Measurement | cm$^3$ * sec/g |

Example

The following are non-limiting examples of the water-absorbing polymer particles of the present invention. The examples are given solely for the purpose of illustration and are not to be construed as limitations of the present invention, as many variations thereof are possible without departing from the spirit and scope of the invention, which would be recognized by one of ordinary skill in the art.

Examples A1 to A4 represents examples of water-absorbing polymer particles according to the invention.

Comparative examples C1 to C3 represents comparative examples of water-absorbing polymer particles.

Chemicals:

Preparation of Deionized Water (>5 MΩ Cm at 25° C.) and Ice Made from Deionized Water:

Quality check: A sample of about 100 g of the ice is melted in a beaker (e.g. 250 ml glass beaker from VWR, LENZ07001049) and the conductivity is measured (e.g. via COND 70 INSTRUMENT without CELL, #50010522, equipped with Cell VPT51-01 C=0.1 from xs instruments or via LF 320/Set, #300243 equipped with TetraCon 325 from WTW), conductivity is <1.6 µS/cm at 0° C.

Montmorillonite suspension in deionized water (solid content about 3.8% wt)

Laponite XL21 (BYK, Germany) suspension in deionized water (solid content about 4% wt)

Preparation of Montmorillonite PGV 3.8 wt % Suspension in Deionized Water (Used for Comparative Example C2 and Comparative Example C3 Preparation).

Chemicals:

Deionized water—>5 MΩ cm at 25° C.

Ice made from deionized water—Quality check: A sample of about 100 g of the ice is melted in a beaker (e.g. 250 ml glass beaker from VWR, LENZ07001049) and the conductivity is measured (e.g. via COND 70 INSTRUMENT without CELL, #50010522, equipped with Cell VPT51-01 C=0.1 from xs instruments or via LF 320/Set, #300243 equipped with TetraCon 325 from WTW), conductivity is <1.6 µS/cm at 0° C.

Montmorillonite Suspension in Deionized Water (Solid Content about 3.8 wt %):

a) Purification:

Montmorillonite PGV® powder (by Nanocor) was suspended in deionized water to form a suspension (PGV at 5 wt %) and magnetically stirred at e.g. 250-600 RPM until no clumps are left and a visually homogeneous suspension was obtained. Na$_4$EDTA was added in portions to a final concentration of 0.1 M of Na$_4$EDTA in the suspension. The clay suspension was then stirred at about 55° C. for two hours, e.g. via a magnetic stir bar at e.g. 250-600 RPM. In order to remove the formed EDTA-metal complexes and excessive EDTA salt, the suspension was dialyzed against deionized water. The progress of the dialysis was controlled by measuring the conductivity of the deionized water (using a typical conductometer, e.g. COND 70 INSTRUMENT without CELL, #50010522, equipped with Cell VPT51-01 C=0.1 from xs instruments or via LF 320/Set, #300243 equipped with TetraCon 325 from WTW). The dialysis was ended when the conductivity decreased below 30 µS/cm. Fresh Na$_4$EDTA (in amount to achieve 0.1 M of Na$_4$EDTA in the suspension) was added and the pH of the mixture was adjusted to pH=8 at room temperature by dropwise addition of 0.01 M HCl (aqueous solution, e.g. from Sigma Aldrich, CAS #7647-01-0). The clay dispersion was stirred at about 55° C. for two hours, e.g. via a magnetic stir bar at e.g. 250-600 RPM. The dialysis was conducted again as above and ended when the conductivity decreased below 30 µS/cm.

Sodium citrate (CAS #6132-04-3, e.g. from Sigma-Aldrich, for molecular biology, #71402) was added as solid to the PGV® suspension (to a final concentration in the mixture of 0.3 M in citrate). The suspension was buffered with 5 ml 1M sodium bicarbonate (aqueous solution, CAS #144-55-8, e.g. from Sigma-Aldrich, for molecular biology, #S5761) per 40 ml 0.3 M citrate solution. The suspension was heated to 80° C. 1 g sodium dithionite (CAS #7775-14-6) per g PGV was added and the suspension was stirred at 80° C. for one hour, e.g. via a magnetic stir bar at e.g. 250-600 RPM. The color of the suspended clay changed from beige to green. After cooling the suspension to room temperature, just enough sodium chloride (CAS #7647-14-5, e.g. from Sigma-Aldrich, for molecular biology, #S3014) was added to provoke flocculation of the clay. Flocculation allows centrifugation of the clay. Therefore, centrifugation was carried out at 3700 RPM for ten minutes with the device Multifuge 1 L (from Heraeus). The clay dispersion was washed once via centrifugation to remove most part of the unreacted dithionite. After centrifugation the dispersion was dialyzed again as described above in deionized water in order to remove the citrate complex and excessive citrate and dithionite, till the conductivity decreased below 30 µS/cm.

The PGV® suspension was purged with ozone produced by an ozonizer (e.g. OZON/Ozon Generator 500 from Fischer) for three days.

b) Concentration:

The purified PGV® suspension (after the last step, the concentration is about 2 wt % of PGV) is concentrated to up to 3.8 wt %. by rotation evaporation (e.g. Heidolph, Type Hei-VAP Value equipped with a Vacuubrand pump (e.g. Vacuubrand GmbH, Germany), type PC 5/MZ 2C) at 45° C. and 60 mbar reduced pressure.

Preparation of the Base Polymers in Order to Obtain Precursor Polymers for Comparative Example C2 and Comparative Example C3 (Base Polymer AS140):

Montmorillonite (PGV® from BYK, Germany) containing BP Synthesis—"BP AS140"

A 5 000 mL resin kettle (equipped with a four-necked glass cover closed with septa, suited for the introduction of a thermometer and syringe needles) is charged with about 350.0 g of ice (ice prepared from deionized water). A magnetic stirrer, capable of mixing the whole content (when liquid), is added and stirring is started (e.g. elliptic magnetic stir barr from VWR, #442-0507). Stirring can take place e.g. at 250-600 RPM.

320.3 g of deionized water is taken to dissolve 5.884 g of "PEG700-DA" (e.g. poly(ethylene glycol)-diacrylate with number average molecular weight of about 700 g/mol, from Sigma-Aldrich, CAS #26570-48-9) e.g. in a glass vessel with plastic snap-on cap (e.g. from VWR, #216-1777). The vessel with the "PEG700-DA" solution is closed and set aside.

50.0 g of deionized water is taken to dissolve 0.686 g of "KPS" (e.g. potassium persulfate from Sigma-Aldrich, CAS #7727-21-1) e.g. in a glass vessel with plastic snap-on cap (e.g. from VWR, #216-1777). To this solution, about 0.22 g of 1% wt. aqueous solution of hydrogen peroxide (prepared by dilution with deionized water of 30% wt. aqueous hydrogen peroxide solution obtained from Sigma-Aldrich CAS #7722-84-1), are added. The so obtained mixture "KPS" solution is closed and set aside. This solution must be used within 6 hours of preparation.

5.0 g of deionized water is taken to dissolve 0.149 g of ascorbic acid (from Sigma-Aldrich, CAS #50-81-7) e.g. in a 20 mL glass vial with a plastic cap. The solution "ascorbic acid" is closed and set aside.

A "Clay" mixture is obtained as follows: about 296.855 g of PGV® suspension of 3.8% wt. (i.e. Montmorillonite suspension in water—see above description) (are charged to a beaker of 500 mL volume and stirred magnetically (e.g. with e.g. elliptic magnetic stir bar from VWR, #442-0507 or the like) at about 200-400 rpm, while about 6.345 g of "ODD" are added (ethoxylated polyethyleneimine ODD e.g. Sokalan HP20, from BASF, CAS #68130-99-4). To decrease the viscosity, about 50.0 g of deionized water are added. The so obtained "Clay" mixture is stirred at about 200-400 rpm until needed.

605.6 g of glacial acrylic acid (AA, CAS #79-10-7; Acrylic Acid for synthesis, from Merck, #800181) is added to the ice in the resin kettle while stirring is continued.

A thermometer is introduced into the resin kettle and in total 457.3 g of 50 w % NaOH solution (for analysis, from Merck, #158793, CAS #1310-73-2) and about 50.0 g of ice (prepared from de-ionized water) are added subsequently in portions such that the temperature is in the range of about 15-30° C. The mixture is continuously stirred.

The "PEG700-DA" solution is added to the mixture of acrylic acid (AA), NaOH solution and ice at a temperature of about 15-30° C. while stirring is continued. The vessel that contained the "PEG700-DA" solution is washed twice with deionized water in an amount of about 3% of the "PEG700-DA" solution volume per wash. The wash water of both washing steps is added to the stirred mixture.

The "Clay" mixture is added to the mixture of acrylic acid (AA), NaOH solution, ice and "PEG700-DA" at a temperature of about 15-30° C. while stirring is continued. The vessel that contained the "Clay" solution is washed two times with deionized water in an amount of about 5% of the "Clay" solution volume per wash. The wash water of both washing steps is added to the stirred mixture.

Deionized water (the remaining amount required to achieve the total amount of (ice+water) of 940.8 g is added to the stirred mixture, e.g. ca. 111.1 g of deionized water.

Then, the resin kettle is closed, and a pressure relief is provided e.g. by puncturing two syringe needles through the septa. The solution is then purged vigorously with argon via an injection needle (stainless steel 304 syringe, 36 inches long, size 16 gauge from Sigma-Aldrich, #Z152404-1EA) at about 0.4 bar while stirring at about 250-600 RPM. The argon stream is placed close to the stirrer for efficient and fast removal of dissolved oxygen.

After about minimum 1 hour and maximum 2 hours of Argon purging and stirring, the "ascorbic acid" solution is added to the reaction mixture at a temperature of about 20-25° C. via a syringe while stirring and Argon purging is continued. Within 1 min, the "KPS" solution is also added via funnel through one of the 4 necks in the glass cover, which is quickly covered after the addition of "KPS" is completed.

After the initiator solutions ("ascorbic acid" and "KPS" solutions) are mixed with the reaction mixture, stirring and Argon purging is continued and temperature is recorded. As the polymerization starts, indicated by temperature raise in small steps, and more specifically after the gel point, characterized by sudden increase in viscosity, stirring is stopped and the purging needle is moved above the reaction mixture. The temperature is monitored; typically it rises from about 23° C. to about 70-90° C. within 60 minutes. Once the temperature reaches a maximum (the reaction mixture can reach for example up to about 100° C.) and starts dropping, the resin kettle is transferred into a circulation oven (Binder FED 720) and kept at about 60° C. for about 20 hours.

Preparation of the Base Polymers in Order to Obtain Precursor Polymers for Examples A1, A2, A3, A4 and Comparative Example C1

Aqueous Laponite suspension preparation:

"Laponite XL21" 4.0 wt % suspension in deionized water is prepared by mixing e.g. 50 g of dry Laponite XL21 (CAS #85085-18-3, from BYK Additives GmbH, Moosburg, Germany) gradually into 1 200.0 g of deionized water while vigorously stirring with magnetic bar (e.g. from VWR, #442-0507) at about 400-600 rpm. The 4.0 wt % suspension is left stirring for about 15 hours to allow for uniform suspension of clay, which is manifested by increasing viscosity, disappearance of visible clay aggregates and uniform translucence of the suspension.

Preparation of Base Polymers for Example A1 (Base Polymer AS170):

A 5 000 mL resin kettle (equipped with a four-necked glass cover closed with septa, suited for the introduction of a thermometer and syringe needles) is charged with about 350.0 g of ice (ice prepared from deionized water). A magnetic stirrer, capable of mixing the whole content (when liquid), is added and stirring is started (e.g. elliptic magnetic stir bar from VWR, #442-0507). Stirring can take place e.g. at 250-600 RPM.

60.0 g of deionized water is taken to dissolve 3.35 g of "PEG700-DA" (e.g. poly(ethylene glycol)-diacrylate with number average molecular weight of about 700 g/mol, from Sigma-Aldrich, CAS #26570-48-9) e.g. in a glass vessel with plastic snap-on cap (e.g. from VWR, #216-1777). The vessel with the "PEG700-DA" solution is closed and set aside.

50.0 g of deionized water is taken to dissolve 0.518 g of "KPS" (e.g. potassium persulfate from Sigma-Aldrich, CAS #7727-21-1) e.g. in a glass vessel with plastic snap-on cap (e.g. from VWR, #216-1777). To this solution, about 0.19 g of 1% wt. aqueous solution of hydrogen peroxide (prepared by dilution with deionized water of 30% wt. aqueous hydrogen peroxide solution obtained from Sigma-Aldrich CAS #7722-84-1). The so obtained mixture "KPS" solution is closed and set aside. This solution must be used within 6 hours of preparation.

10.0 g of deionized water is taken to dissolve 0.114 g of ascorbic acid from Sigma-Aldrich, CAS #50-81-7) e.g. in a 20 mL glass vial with a plastic cap. The solution "ascorbic acid" is closed and set aside.

A "Clay" mixture is obtained as follows: about 213.3 g of 4 wt % "Laponite XL21" suspension (described above), are charged to a beaker of 500 mL volume and stirred magnetically at about 200-400 rpm (e.g. with e.g. elliptic magnetic stir barr from VWR, #442-0507 or the like) while about 4.9 g of "ODD" are added (ethoxylated polyethyleneimine ODD e.g. Sokalan HP20, from BASF CAS #68130-99-4). To decrease the viscosity, about 100.0 g of deionized water are added. The so obtained "Clay" mixture is stirred at said rpm until needed.

460.0 g of glacial acrylic acid (acrylic acid AA, CAS #79-10-7; Acrylic Acid for synthesis, from Merck, #800181) is added to the ice in the resin kettle while stirring is continued.

A thermometer is introduced into the resin kettle and in total 347.2 g of 50 w % NaOH solution (for analysis, from Merck, #158793, CAS #1310-73-2) and about 250.0 g of ice (prepared from de-ionized water) are added subsequently in portions such that the temperature is in the range of about 15-30° C. The mixture is continuously stirred.

The "PEG700-DA" and "Clay" solutions are added according to the description for the Base Polymer synthesis of comparative examples C2 and C3 above.

Deionized water (the remaining amount required to achieve the total amount of (ice+water) of 970.791 g is added to the stirred mixture, e.g. ca. 80.0 g of deionized water.

The execution of the synthesis continues up to obtaining the native polymer in the same manner as described for the Base Polymer synthesis of comparative examples C2 and C3 above.

Preparation of Base Polymers for Example A2 (Base Polymer AS169):

A 5 000 mL resin kettle (equipped with a four-necked glass cover closed with septa, suited for the introduction of a thermometer and syringe needles) is charged with about 534 g of ice (ice prepared from deionized water). A magnetic stirrer, capable of mixing the whole content (when liquid), is added and stirring is started (e.g. elliptic magnetic stir bar from VWR, #442-0507). Stirring can take place e.g. at 250-600 RPM.

60.0 g of deionized water is taken to dissolve 4.47 g of "PEG700-DA" (e.g. poly(ethylene glycol)-diacrylate with number average molecular weight of about 700 g/mol, from Sigma-Aldrich, CAS #26570-48-9) e.g. in a glass vessel with plastic snap-on cap (e.g. from VWR, #216-1777). The vessel with the "PEG700-DA" solution is closed and set aside.

50.0 g of deionized water is taken to dissolve 0.518 g of "KPS" (e.g. potassium persulfate from Sigma-Aldrich, CAS #7727-21-1) e.g. in a glass vessel with plastic snap-on cap (e.g. from VWR, #216-1777). To this solution, about 0.3 g of 1% wt. aqueous solution of hydrogen peroxide (prepared by dilution with deionized water of 30% wt. aqueous hydrogen peroxide solution obtained from Sigma-Aldrich CAS #7722-84-1). The so obtained mixture "KPS" solution is closed and set aside. This solution must be used within 6 hours of preparation.

10.0 g of deionized water is taken to dissolve 0.112 g of ascorbic acid from Sigma-Aldrich, CAS #50-81-7) e.g. in a 20 mL glass vial with a plastic cap. The solution "ascorbic acid" is closed and set aside.

A "Clay" mixture is obtained as follows: about 213.2 g of stock "Laponite XL21" suspension of 4% wt., are charged to a beaker of 500 mL volume and stirred magnetically at about 200-400 rpm (e.g. with e.g. elliptic magnetic stir barr from VWR, #442-0507 or the like) while about 4.8 g of "ODD" are added (ethoxylated polyethyleneimine ODD e.g. Sokalan HP20, from BASF CAS #68130-99-4). To decrease the viscosity, about 100.0 g of deionized water are added. The so obtained "Clay" mixture is stirred at said rpm until needed.

460.0 g of glacial acrylic acid (acrylic acid AA, CAS #79-10-7; Acrylic Acid for synthesis, from Merck, #800181) is added to the ice in the resin kettle while stirring is continued.

A thermometer is introduced into the resin kettle and in total 347.3 g of 50 w % NaOH solution (for analysis, from Merck, #158793, CAS #1310-73-2) and about 250.0 g of ice (prepared from deionized water) are added subsequently in portions such that the temperature is in the range of about 15-30° C. The mixture is continuously stirred.

The "PEG700-DA" and "Clay" solutions are added according to the description for the Base Polymer synthesis of comparative examples C2 and C3 above Deionized water (the remaining amount required to achieve the total amount of (ice+water) of 969.642 g is added to the stirred mixture, e.g. ca. 80.0 g of deionized water.

The execution of the synthesis continues up to obtaining the native polymer in the same manner as described for the Base Polymer synthesis of comparative examples C2 and C3 above Preparation of Base Polymers for Examples A3 and A4-Base Polymer AS220

A 20 000 mL resin kettle (equipped with a four-necked glass cover closed with septa, suited for the introduction of a thermometer and syringe needles) is charged with about 2167 g of ice (ice prepared from deionized water). A magnetic stirrer, capable of mixing the whole content (when liquid), is added and stirring is started (e.g. elliptic magnetic stir bar from VWR, #442-0507). Stirring can take place e.g. at 250-600 RPM.

500 g of deionized water is taken to dissolve 44.60 g of "PEG700-DA" (e.g. poly(ethylene glycol)-diacrylate with number average molecular weight of about 700 g/mol, from Sigma-Aldrich, CAS #26570-48-9) e.g. in a glass vessel with plastic snap-on cap (e.g. from VWR, #216-1777). The vessel with the "PEG700-DA" solution is closed and set aside.

200 g of deionized water is taken to dissolve about 5.18 g of "KPS" (e.g. potassium persulfate from Sigma-Aldrich, CAS #7727-21-1) e.g. in a glass beaker of 250 ml volume. To this solution, about 0.19 g of 1% wt. aqueous solution of hydrogen peroxide (prepared by dilution with deionized water of 30% wt. aqueous hydrogen peroxide solution obtained from Sigma-Aldrich CAS #7722-84-1). The so obtained mixture "KPS" solution is closed and set aside. This solution must be used within 6 hours of preparation.

20.0 g of deionized water is taken to dissolve 1.124 g of ascorbic acid (e.g. from Sigma-Aldrich, CAS #50-81-7) e.g. in a 20 mL glass vial with a plastic cap. The solution "ascorbic acid" is closed and set aside.

A "Clay" mixture is obtained as follows: about 2108.8 g of 4 wt % "Laponite XL21" suspension (described above), are charged to a beaker of 2,500 mL volume and stirred magnetically at about 200-400 rpm (e.g. with e.g. elliptic magnetic stir bar from VWR, #442-0507 or the like) while about 48.0 g of "ODD" are added (ethoxylated polyethyleneimine ODD, e.g. Sokalan HP20, from BASF CAS #68130-99-4). To decrease the viscosity, about 1000.0 g of deionized water are added. The so obtained "Clay" mixture is stirred at said rpm until needed.

4600.0 g of glacial acrylic acid (acrylic acid AA, CAS #79-10-7; Acrylic Acid for synthesis, from Merck, #800181) is added to the ice in the resin kettle while stirring is continued.

A thermometer is introduced into the resin kettle and in total 3472.70 g of 50 w % NaOH solution (for analysis, from Merck, #158793, CAS #1310-73-2) and about 6878.4 g of ice (prepared from deionized water) are added subsequently in portions such that the temperature is in the range of about 15-30° C. The mixture is continuously stirred.

The "PEG700-DA" and "Clay" solutions are added according to the description for the Base Polymer synthesis of comparative examples C2 and C3 above Deionized water (the remaining amount required to achieve the total amount of (ice+water) of 9694.3 g is added to the stirred mixture, i.e. ca. 649 g of deionized water.

The execution of the synthesis continues up to obtaining the native polymer in the same manner as described for the Base Polymer synthesis of comparative examples C2 and C3 above Preparation of Base Polymers for Comparative Example C1-Base Polymer AS204

A 5 000 mL resin kettle (equipped with a four-necked glass cover closed with septa, suited for the introduction of a thermometer and syringe needles) is charged with about 350.0 g of ice (ice prepared from deionized water). A magnetic stirrer, capable of mixing the whole content (when liquid), is added and stirring is started (e.g. elliptic magnetic stir bar from VWR, #442-0507). Stirring can take place e.g. at 250-600 RPM.

60.0 g of deionized water is taken to dissolve 8.06 g of "PEG700-DA" (e.g. poly(ethylene glycol)-diacrylate with number average molecular weight of about 700 g/mol, from Sigma-Aldrich, CAS #26570-48-9) e.g. in a glass vessel with plastic snap-on cap (e.g. from VWR, #216-1777). The vessel with the "PEG700-DA" solution is closed and set aside.

50.0 g of deionized water is taken to dissolve 0.516 g of "KPS" (e.g. potassium persulfate from Sigma-Aldrich, CAS #7727-21-1) e.g. in a glass vessel with plastic snap-on cap (e.g. from VWR, #216-1777). To this solution, about 0.2 g of 1% wt. aq. solution of hydrogen peroxide (prepared by dilution with deionized water of 30% wt. aq. hydrogen peroxide solution obtained from Sigma-Aldrich CAS #7722-84-1). The so obtained mixture "KPS" solution is closed and set aside. This solution must be used within 6 hours of preparation.

10.0 g of deionized water is taken to dissolve 0.112 g of ascorbic acid (e.g. from Sigma-Aldrich, CAS #50-81-7) e.g. in a 20 mL glass vial with a plastic cap. The solution "ascorbic acid" is closed and set aside.

A "Clay" mixture is obtained as follows: about 214.5 g of "Laponite XL21" suspension of 4% wt., are charged to a beaker of 500 mL volume and stirred magnetically (e.g. with e.g. elliptic magnetic stirbar from VWR, #442-0507 or the like) while about 4.8 g of "ODD" are added (ethoxylated polyethyleneimine ODD, e.g. Sokalan HP20, from BASF CAS #68130-99-4). To decrease the viscosity, about 100.0 g of deionized water are added. The so obtained "Clay" mixture is stirred until needed.

459.9 g of glacial acrylic acid (AA, CAS #79-10-7; Acrylic Acid for synthesis, from Merck, #800181) is added to the ice in the resin kettle while stirring is continued.

A thermometer is introduced into the resin kettle and in total about 347.3 g of 50 w % NaOH solution (for analysis, from Merck, #158793, CAS #1310-73-2) and about 250.0 g of ice (prepared from de-ionized water) are added subsequently in portions such that the temperature is in the range of about 15-30° C. The mixture is continuously stirred.

The "PEG700-DA" and "Clay" solutions are added according to the description for the Base Polymer synthesis of comparative examples C2 and C3 above Deionized water (the remaining amount required to achieve the total amount of (ice+water) of 964.38 g is added to the stirred mixture, e.g. ca. 109.0 g of deionized water.

The execution of the synthesis continues up to obtaining the native polymer in the same manner as described for the Base Polymer synthesis of comparative examples C2 and C3 above Post-Polymerization Treatment of Native Polymers to A1 Through A4 and C1 Through C3

After the polymerization completion time in the circulation oven, the latter is switched off and the resin kettle is allowed to cool down to about 20° C. to 40° C. while remaining in the oven. After that, the gel is removed and broken manually or cut with scissors into smaller pieces. The gel is ground with a grinder (X70G from Scharfen with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (e.g. Binder FED 720) equipped with a condensate trap from DAMM (condensation via cooling below dew point via heat exchanger) to dry the circulation air, cooled to 5° C. via a thermostat (Julabo FP 50)) at about 120° C. for about 20 hours.

The dried gel is then ground using a centrifuge mill (e.g. Retsch ZM 200 with vibratory feeder DR 100 (setting 50-60), interchangeable sieve with 1.5 mm opening settings, rotary speed 8000 rpm). The milled polymer is again dried in an oven (e.g. Binder FED 720) for 12 hours at 120° C. and then sieved via a sieving machine (e.g. AS 400 control from Retsch with sieves DIN/ISO 3310-1 of 150 um and 710 um at about 200-280 rpm for about for 5-10 min) to a sieve cut which contains >95% wt. of the materials between 150 and 850 microns to obtain the Base Polymers for A1 through A4 and C1 through C3

Surface Crosslinking Treatment of Native Polymers in Order to Obtain Examples A2, A3, A4 and Comparative Examples C1 and C2

Equipment List:
- Glassware, one way pipette, spatula, spoon to prepare solution and weigh in absorbent materials
- Beaker: 250 ml opening ø 70 mm
- Balance: Sartorius or equivalent; accuracy 0.01 g
- Analytical balance: Mettler or equivalent; accuracy 0.0001 g
- Electrical stand stirrer: IKA Eurostar power control visc (Range 50-2000 rpm) or equivalent With Stirrer: PTFE Propeller stirrer 4-bladed_ø50 mm
Pipette: Eppendorf Multi stream or equivalent
Aluminum foil for covering
Circulation oven: Binder FD 240 or equivalent
Equipment to determine Moisture: Halogen Moisture Balance Mettler or equivalent
Sieve machine: Retch AS 200 control "g" or equivalent
With Sieves: stainless steel: DIN/ISO 3310-1 ø10 mm
Preparation of Solution:
Aluminum lactate solution
Prepare 1 kg 15 w % Aluminum lactate solution in deionized water (MilliporeQ of conductivity <1.6 µS/cm) by adding 850 g of deionized water to 150 g of Aluminum lactate.

Surface crosslinking solutions (SXL solutions) (see table 2):

The used Denacol concentrations are prepared according to table 2, each in snap cap jars of volume about 50 ml.

To prepare the solutions, the Denacol bottle or container (ca. 1 l) is taken out of the fridge and let to stay out to thermally equilibrate for ca. 30 min before preparing the solutions.

Solutions are prepared as follows:

Different respective concentrations, for the given examples, of Denacol (e.g. Denacol EX810, DN-810) are prepared by adding the amount shown in Table 2 to the snap cap plastic jar which is then filled to 20 g with 1,2-Propanediol.

TABLE 2

| Surface crosslinking agent | Examples/ comparative examples | Concentration (in wt. %) | Preparation of solution |
| --- | --- | --- | --- |
| Denacol - Ex810 | A2, C2 | 18% | 3.6 g DN-810 filled in with 1,2 Propanediol to 20 g |
| Denacol - Ex810 | A3 | 8% | 1.6 g DN-810 filled in with 1,2 Propanediol to 20 g |
| Denacol - Ex810 | A4 | 12% | 2.4 g DN-810 filled in with 1,2 Propanediol to 20 g |
| Denacol - Ex810 | C1 | 10% | 2.0 g DN-810 filled in with 1,2 Propanediol to 20 g |

Execution of SXL Procedure:

Each of the respective absorbent material (e.g. dry Base Polymers) is weighed to be 20-30 g and recorded to ±0.1 g and placed in a separate 250 ml glass beaker so that the filling height is ≤25% of the overall height. Exact amounts are given in Table 4.

The water-absorbing polymer particles are mixed it at 600+/−50 rpm with a PTFE stirrer into the beaker. The stirrer is just touching the bottom of the beaker. The water-absorbing polymer particles need to be stirred until good fluidization of the bed is achieved.

The requested amounts of solutions are added with an Eppendorf pipette, step by step like described below and the actual quantities are given in Table 3. (Speed setting of Eppendorf pipette: Middle speed)

Step 1:

The amount of Aluminum Lactate Solution is added into the center of stirring agitation. Afterwards, the stirring speed is to be raised to 2000+/−50 rpm. Stir for approximately 15 seconds and continue with Step 2. If necessary, cover beaker with e.g. aluminum foil to avoid jumping out of material.

Step 2:

The amount of SXL solution is added into the center of stirring agitation. Stir for approximately 15 seconds and continue with Step 3.

Step 3:

Amount of deionized water (3 wt % vs. sample weight) is added into the center of stirring agitation. Stir for approximately 15 seconds. After stopping stirrer transfer the material into a heat resistant wide-mouth glass vial (e.g. crystallizing dish) and distribute it evenly. Take loose material only and leave strong stacked material on wall in beaker. Remove loose material by slight tapping outside on wall of beaker or by use of spatula. Avoid scratching out. Cover the wide mouth glass vial with aluminum foil and store it into a fume hood at room temperature for approximately 16 h to 18 h (overnight is recommended) and afterwards heat the material in the oven at requested temperature and time (e.g. Surface crosslinking Denacol heat up period of 20 min from room temperature to 120° C. in addition to the 2 h heating time).

After heating time, remove container from the oven and open the aluminum foil half-way. Place the material into a fume hood to cool down to room temperature, for approximately 15 min.

The final polymers were tested for moisture.

TABLE 3

| Example | Moisture, wt % |
| --- | --- |
| A2 | 0.6 |
| A3 | 0.6 |
| A4 | 0.6 |
| C1 | 0.6 |
| C2 | 0.7 |

TABLE 4

| Examples and comparative examples | Amount of Base Polymer treated (in g) | Denacol Ex810 concentration, (in wt %) | Overall Denacol Ex810 add-on vs. polymer (in wt %) | Overall Aluminium lactate add-on vs polymer, (in wt %) | Added deionized water (in wt % vs polymer) |
| --- | --- | --- | --- | --- | --- |
| A2 | 20.0 | 18 | 0.18 | 0.9 | 3 |
| A3 | 30.0 | 8 | 0.08 | 0.9 | 3 |
| A4 | 30.0 | 12 | 0.12 | 0.9 | 3 |
| C1 | 20.0 | 10 | 0.1 | 0.9 | 3 |
| C2 | 25.0 | 18 | 0.18 | 0.9 | 3 |

The quantities of Denacol Ex810 are selected such that the resulting examples and comparative examples exhibit CRC above 25 g/g and EFFC between 23 and 28 g/g (see table 5)

Surface Crosslinking Treatment with Primid XL 552 of Native Polymers in Order to Obtain Example A1 Surface Crosslinker Application in Fluidized Bed Lab Conditions Ambient conditions of 23±2° C. and relative humidity of 45±10%.

Surface Crosslinking Chemicals:

Primid® XL-552, β-hydroxylalkylamide (CAS 6334-25-4, e.g. from EMS-CHEMIE AG)

Aluminum L-lactate (CAS 18917-91-4, e.g. from Sigma-Aldrich #430633) Equipment:

ProCell Labsystem Pro by Glatt Ingenieurtechnik GmbH with the Coater Module GF3 (reactor [B206010] with process insert [B203010]) with the transitional housing [B203000] and Wurster insert (70 mm diameter and 190 mm height)) with Wurster bottom "Type B" and cyclone [F121490]; or similar equipment.

The spray nozzle is a two-stream bottom spray nozzle (Schlick two-stream nozzle, model #970form0S4). Nozzle cap position is adjusted to flush with the tip of the nozzle pipe.

Project number: W51505 in 2013.

The system is run without feedback stream of fines from the cyclone.

Pump: Ismatec pump ISM 404B, with pump head ISM 720A.

Hose: silicon peroxid ID=2.06 mm, VWR #228-0704.

Preparation of 1 kg Surface Crosslinker Solution 30.0 g of Aluminum L-lactate is added to a glass beaker equipped with a magnetic stir bar. 20.0 g of Primid® XL-552 is added and deionized water (e.g. MilliporeQ, conductivity <1.6 µS/cm) is added to obtain the total weight of the solution of 1000.0 g±5.0 g. The solution is stirred with a magnetic bar at e.g. 250-600 RPM until the solid substances are dissolved and clear solution is obtained.

Equipment Preparation:

Before the coating is started, the equipment is closed, started and the pressured air valve is opened. The equipment is preheated for about 15 min with air flow of 100 Nm$^3$/h at 80° C. set point for fluidization air.

Pump calibration: The peristaltic pump with the silicon hose is calibrated with about 20 g of the of Aluminum L-lactate/Primid® XL-552 solution (flow rate 2.0 g/min±0.1 g/min).

Coating:

240.0 g±1.0 g of base-polymer particles of example A1 is placed in the GF3 process vessel.

The equipment is closed, and the equipment is started in the following order at the respective settings:

1) The fan is started, setting 65 Nm$^3$/h, fluidization air temperature 45° C.

2) The nozzle air is started at 1.2 bar spray pressure.

3) When the temperature inside the coating vessel has reached about 45° C., the liquid port of the spray nozzle is connected via the hose mounted in the pump head to the Aluminum L-lactate/Primid® XL-552 solution and the pump is started. The solution is sprayed at a spray rate of about 2.0 g/min±0.1 g/min onto the base-polymer particles of example A1 in the reactor. For the duration of the experiment, the fluidization air temperature is controlled within the range from 43° C. to 47° C. and the fluidization air flow rate within 60 and 70 m$^3$/h. It is important that the spray rate of the coating agent, the fluidization air temperature and fluidization air flowrate are set such that the water-absorbing polymer particles are not getting sticky and no additional drying is needed after the coating is completed.

In total, 120.0 g±1.0 g of surface cross-linker solution is sprayed onto the base-polymer particles of example A1 during coating. After that, the equipment is stopped as following:

1) The heater is stopped.

2) The fan is stopped.

3) The spray air of the nozzle is stopped.

4) The coated water-absorbing polymer particles are discharged from the reactor into a stainless steel bowl and weight to the nearest 0.1 g. In case the weight of discharged coated water-absorbing polymer particles deviates more than 15 w % from the in-weight of base-polymer particles of example A1 (here 240.0 g±1.0 g) the material is discarded and the experiment needs to be repeated.

Water Addition Process:

Chemicals:

Deionized water: >5 MΩ cm at 25° C.

30.0±0.1 g of coated water-absorbing polymer particles are placed in a glass beaker with 250 ml capacity (e.g. 250 ml glass beaker from VWR, LENZ07001049, with diameter of about 10 cm). The coated water-absorbing polymer particles inside the beaker are stirred with a 4-bladed PTFE coated propeller mixer (e.g. IKA Labmixer EUROSTAR 400). The propeller is rotating with about 2000 RPM. A pipette (e.g. Eppendorf Xplorerg or Eppendorf Multistreamg) is loaded with 1.800 ml±0.01 ml of deionized water.

The stirrer is started already before the water is added. The pipette is discharged into the vessel onto the stirred bed of particles at once (approximately halfway between the beaker wall and the stirrer shaft. For the performance, it is critical that the water is uniformly distributed onto the coated water-absorbing polymer particles. The stirring continues for about 15 s and the content of the vessel is transferred into a 500 ml flat glass dish with diameter of about 12 cm. The coated water-absorbing polymer particles are distributed evenly on the bottom of this glass dish. The glass dish is covered with an aluminum foil and transferred into a circulation oven (e.g. Binder FED 720 available from Binder GmbH, Tuttlingen, Germany). The oven has been preheated to 160° C. The temperature in the oven is controlled within the range from 155 to 165° C. The coated water-absorbing polymer particles stay inside the oven for about 2 h and 20 mins. coated water-absorbing polymer particles is removed from the oven, remains in the aluminum foil covered dish and is let cooled down to room temperature.

After the coated water-absorbing polymer particles are cooled to room temperature, they are sieved via sieves of about 20 cm in diameter (available e.g. from Retsch GmbH, Haan, Germany; DIN/ISO 3310-1). A stack of sieves with the following mesh sizes (sequence from top to bottom) is used: 710 µm, 150 µm and collecting pan. The superabsorbent particles sample is loaded to the top sieve (i.e. 710 µm) and sieved via a sieve machine (e.g. "AS 00 control 'g'" available from Retsch GmbH, Haan, Germany) for 3 min at 1 mm/'g'.

The fraction of coated water-absorbing polymer particles of the size from 150 µm to 710 µm represents the sample A1. The moisture level of sample A1 is 0.5 wt %.

Surface crosslinking treatment of native polymer of comparative example C3 in beaker in order to obtain comparative example C3 with Denacol Ex810 (e.g. Ethylene Glycol DiGlycidyl Ether=EGDGE, from Nagase, Japan)

The dried classified native polymer of comparative example C3 was surface-crosslinked as following to obtain comparative example C3.

Preparation of 10 g 0.5 wt % of Denacol Ex810 Solution in Deionized Water:

0.05 g of Denacol Ex810 is added to a 50 ml glass beaker equipped with a magnetic stir bar. Deionized water (e.g. MilliporeQ, conductivity <1.6 µS/cm) is added to obtain the total weight of the solution of 10.0 g±0.1 g. The solution is stirred with a magnetic bar at e.g. 250-300 RPM for about 1 min until clear solution is obtained.

Preparation of 10 g 15 wt % of Aluminum Lactate Solution 1.50 g of Aluminum L-lactate is added to a glass beaker equipped with a magnetic stir bar. Deionized water (e.g. MilliporeQ, conductivity <1.6 µS/cm) is added to obtain the total weight of the solution of 10.0 g±0.1 g. The solution is stirred with a magnetic bar at e.g. 250-300 RPM until the solids are dissolved and clear solution is obtained.

About 20.0 g of native polymer of comparative example C3 was weighed into a 250 mL glass beaker with diameter about 10 cm and stirred with a shear mixer at 600 rpm (IKA Werke Eurostar power control visc, equipped with a Teflon-coated 4-bladed propeller of about 40 cm length, head diameter of about 5 cm (from VWR)). First, 1.60 g 15% wt aqueous solution of Aluminum lactate (Sigma-Aldrich, CAS #18917-91-4) prepared as described above, is added drop-wise via an Eppendorf pipette ((Eppendorf Xplorer® or Eppendorf Multistream®) to the center of the beaker while stirring. Afterwards, about 2.64 g of the Denacol Ex810 aqueous solution, prepared as described above, is added drop wise to the center of the beaker via an Eppendorf pipette (e.g. Eppendorf Xplorer® or Eppendorf Multistreamg) while stirring. After the addition is accomplished, the mixture is stirred for an additional 1 min until it appears more homogeneous and less caking, Stirring is stopped and the mixture is put into a glass lab dish (e.g. 20×30 cm), covered with aluminum foil and left overnight in the fume hood at room temperature.

The filled & covered lab dish is put into a circulation oven (e.g. Binder FED 720) and kept at 120° C.-140° C. for 2 h (warm up phase after opening the oven (80° C.->120° C.) typically takes 20 min). After 2 h 20 min at 120° C.-140° C., the lab dishes are put under the fume hood and the covering aluminum foil is cut to get 4 openings of ca. 1.5 cm×4 cm. The samples cool down to room temp (e.g. over 1-3 hours). The samples are manually broken and sieved to 150-850 µm to get the final material as follows.

After the coated water-absorbing polymer particles are cooled to room temperature, they are sieved via sieves of about 20 cm in diameter (available e.g. from Retsch GmbH, Haan, Germany; DIN/ISO 3310-1). A stack of sieves with the following mesh sizes (sequence from top to bottom) is used: 850 µm, 150 µm and collecting pan. The coated water-absorbing polymer particles are loaded to the top sieve (i.e. 850 µm) and sieved via a sieve machine (e.g. "AS 00 control 'g'" available from Retsch GmbH, Haan, Germany) for 3 min at 1 mm/'g'.

The fraction of coated water-absorbing polymer particles of the size from 150 µm to 850 µm represents the sample C3. The moisture level of sample C3 is 0.7 wt %.

Results:

TABLE 5

| Sample | $R_{XL}$ at 20 g/g | $R_{XL}$ at 30 g/g | Base polymer CRC (g/g) | D10 (nm) | D50 (nm) | D90 (nm) | AAP (g/g) | CRC (g/g) | EFFC (g/g) | SFC (g/g) | Extractable (in wt %) | Surface Crosslinker concentration (in wt %) |
|---|---|---|---|---|---|---|---|---|---|---|---|---|
| A1 | 16 | 18 | 40.5 | 9 (1) | 14 (1) | 20 (1) | 24.4 | 30.2 | 27.3 | 64 | 6.5 | 1* |
| A2 | 14 | 17 | 40.5 | 9 (1) | 14 (1) | 20 (1) | 24.3 | 27.2 | 25.8 | 137 | 6.3 | 0.18 |
| A3 | 16 | 18 | 37.5 | 9 (1) | 14 (1) | 20 (1) | 22.9 | 32.4 | 27.6 | 8 | 6.9 | 0.08 |
| A4 | 16 | 18 | 37.5 | 9 (1) | 14 (1) | 20 (1) | 23.2 | 30.9 | 27.0 | 18 | 6.9 | 0.12 |
| C1 | 12 | 14 | 32.8 | 9 (1) | 14 (1) | 20 (1) | 24.6 | 27.1 | 25.9 | 85 | 3.3 | 0.1 |
| C2 | 14 | 17 | 36.8 | 180 (2) | 250 (2) | 370 (2) | 21.9 | 25.3 | 23.6 | 137 | 8.9 | 0.18 |
| C3 | 14 | 17 | 36.8 | 180 (2) | 250 (2) | 370 (2) | — | 29.4 | — | 15 | 8.9 | 0.08 |

*Surface crosslinker is Primid XL 552. For the other samples, the surface crosslinker is Denacol Ex810.
(1) Karpovich, A et al, MethodsX, 2016, 3, 19-24, "Dynamic light scattering method, NMR relaxometry method".
(2) Hausner, J, PhD Dissertation "New Concepts in Production of Polymer Composites", University of Bayreuth, Germany, 2015, p. 60

The surface crosslinker add-on levels are chosen such as to reflect the starting base polymer capacity and deliver a CRC in a commercially relevant area of above 25 g/g and EFFC in a range of 23 to 28 g/g.

Comparative example C1 does not fulfill the requirement of the invention. Indeed, the average closest distance between two neighboring crosslinkers (RXL) at 20 g/g X-load of the water-absorbing polymer particle of C1 is lower than the size of the inorganic solid particles that is represented by the D50 value. Moreover, the comparative example C1 comprises a higher concentration of crosslinkers compared to the examples of the invention. That is why; the amount of "extractables" in the water-absorbing polymer particle is lower than for the examples of the invention.

Comparative examples C2 and C3 do not fulfill the requirement of the invention. Indeed, the average closest distance between two neighboring crosslinkers (RXL) at 20 g/g X-load of the water-absorbing polymer particle of C2 and C3 is lower than the size of the inorganic solid particles that is represented by the D50 value. The amount of extractables is higher for comparatives examples C2 and C3 compared to the examples of the invention.

The water-absorbing polymer particles of the invention, i.e. example A1, example A3, example A4, have a high effective capacity values (EFFC) compared to the comparative examples C1 and C2 that do not fulfill the requirement of the invention.

The water-absorbing polymer particles of example A2 shows a high permeability, a good absorption capacity and a good absorption against pressure compared to comparative example C2 which also shows a high permeability.

The water-absorbing polymer particles of examples A1, A3 and A4 show a high absorption capacity and a good effective capacity compared to the comparative examples C1 and C2 even if the permeability value of example A4 is lower compared to the comparative examples.

Moreover, the water-absorbing polymer particles of examples A1, A3 and A4 show a better absorption capacity than comparative example C3.

Therefore, the examples of the invention, i.e. A1 to A5, having an average closest distance between two neighboring crosslinkers (RXL) at 20 g/g X-load of the water-absorbing polymer particle obtained via the formula above being at least as high as an average size of the inorganic solid particles, show good performance properties, especially a high effective capacity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making water-absorbing polymer particles by providing crosslinkers, polymerizable monomers, and inorganic solid particles,
    wherein an average closest distance between two neighboring crosslinkers ($R_{XL}$) in a water-absorbing polymer particle for a specific X-load of the water-absorbing polymer particle is calculated via the formula below:

$$Rxl = \left( \frac{\left( \frac{1}{rho\_dry} + \frac{x\_L}{rho\_liq} \right)}{N_A \cdot \sum_i \frac{w\_xl_i}{Mr\_CXL_i}} \right)^{\frac{1}{3}} \quad (I)$$

with x_L being an amount of liquid absorbed in the water-absorbing polymer particle in $g_{liq}/g_{water-absorbing\ polymer\ particle}$,
rho_liq being a density at room temperature of a fluid that swells the water-absorbing polymer particle in g/cm$^3$, wherein the fluid that swells the water-absorbing polymer particle is saline of 0.9% w NaCl,
rho_dry being a true density of the water-absorbing polymer particle in a dry state in g/cm$^3$,
Mr_CXL being a molar mass of the crosslinkers in g/mol,
w_xl being a weight ratio of the crosslinkers in the water-absorbing polymer particle in the dry state,
$N_A$ being Avogadro's number in mol$^{-1}$,
wherein the average closest distance between two neighboring crosslinkers ($R_{XL}$) at 20 g/g X-load of the water-absorbing polymer particle obtained via the formula above is at least as high as an average size of the inorganic solid particles, and
wherein the average closest distance between two neighboring crosslinkers ($R_{XL}$) at 20 g/g X-load of the water-absorbing polymer particle is from 3 to 100 nm.

2. The method according to claim 1, wherein the average closest distance between two crosslinkers ($R_{XL}$) at 20 g/g X-load of the water-absorbing polymer particle is from 3 to 50 nm.

3. The method according to claim 1, wherein a concentration of crosslinkers ($C_{XL}$) in the water-absorbing polymer particle is from 0.01 to 0.5 mol %.

4. The method according to claim 1, wherein an average range of size of the inorganic solid particles is from 3 to 100 nm.

5. The method according to claim 1, wherein the crosslinkers comprise acrylate or acrylamide groups.

6. The method according to claim 1, wherein the polymerizable monomers are selected from the group consisting of ethylenically unsaturated carboxylic acids or their salts, ethylenically unsaturated phosphonic acids or their salts, ethylenically unsaturated sulfonic acids or their salts, and mixtures thereof.

7. The method according to claim 1, wherein the water-absorbing polymer particles comprise crosslinked polymers of polyacrylic acids or their salts or polyacrylates or derivatives thereof.

8. The method according to claim 1, wherein the inorganic solid particles are clay platelets.

9. The method according to claim 8, wherein the clay platelets are laponite.

10. The method according to claim 1, wherein a concentration of inorganic solid particles in the water-absorbing polymer particles is from 0.1 to 8% by weight compared to a total weight of the water-absorbing polymer particles in the dry state.

11. The method according to claim 1, wherein the water-absorbing polymer particles have a value of Effective Capacity (EFFC) between 25 g/g and 28 g/g according to the EFFC test method.

12. The method according to claim 1, wherein the water-absorbing polymer particles have a value of UPM (Urine Permeability Measurement) of at least 5 UPM units according to the UPM test method.

13. The method according to claim 1, wherein the water-absorbing polymer particles are surface crosslinked.

14. Water-absorbing polymer particles obtained by the method according to claim 1.

15. An absorbent article comprising the water-absorbing polymer particles according to claim 14.

16. The method according to claim 1, wherein a concentration of crosslinkers ($C_{XL}$) in the water-absorbing polymer particle is from 0.02 to 0.25 mol %.

17. The method according to claim 8, wherein the clay platelets are surface and/or edge modified.

* * * * *